United States Patent
Heller et al.

(10) Patent No.: US 9,217,167 B2
(45) Date of Patent: Dec. 22, 2015

(54) LIGASE-ASSISTED NUCLEIC ACID CIRCULARIZATION AND AMPLIFICATION

(71) Applicant: General Electric Company, Schenectady, NY (US)

(72) Inventors: Ryan Charles Heller, Guilderland, NY (US); John Richard Nelson, Clifton Park, NY (US); Erik Leeming Kvam, Albany, NY (US)

(73) Assignee: General Electric Company, Niskayuna, NY (US)

( * ) Notice: Subject to any disclaimer, the term of this patent is extended or adjusted under 35 U.S.C. 154(b) by 179 days.

(21) Appl. No.: 13/952,040

(22) Filed: Jul. 26, 2013

(65) Prior Publication Data

US 2015/0031086 A1  Jan. 29, 2015

(51) Int. Cl.
 *C12P 19/34* (2006.01)
 *C12Q 1/68* (2006.01)

(52) U.S. Cl.
 CPC ............... *C12P 19/34* (2013.01); *C12Q 1/6869* (2013.01)

(58) Field of Classification Search
 CPC C12P 19/34; C12Q 1/6869; C12Q 2521/501; C12Q 2525/307; C12Q 2527/137
 USPC ........................................................ 435/91.2
 See application file for complete search history.

(56) References Cited

U.S. PATENT DOCUMENTS

| | | | |
|---|---|---|---|
| 7,790,388 | B2 | 9/2010 | Landegren et al. |
| 8,003,330 | B2 | 8/2011 | Heiner et al. |
| 2004/0209299 | A1 | 10/2004 | Pinter et al. |
| 2007/0111216 | A1* | 5/2007 | Jendrisak et al. ................ 435/6 |
| 2008/0242560 | A1 | 10/2008 | Gunderson et al. |
| 2010/0297710 | A1 | 11/2010 | Hoyal-Wrightson et al. |
| 2011/0224106 | A1 | 9/2011 | Eshoo et al. |
| 2012/0164691 | A1 | 6/2012 | Eshoo et al. |

FOREIGN PATENT DOCUMENTS

| | | |
|---|---|---|
| EP | 2396430 A1 | 12/2011 |
| WO | 2010094040 A1 | 8/2010 |

OTHER PUBLICATIONS

Weiss et al., "Enzymatic Breakage and Joining of Deoxyribonucleic Acid—Properties of the Enzyme-Adenylate Intermediate in the Polynucleotide Ligase Reaction", The Joumvnr, of Biological CIIE-Stry, vol. 243, No. 17, Issue of Sep. 10, 1968, pp. 4556-4563.

Shore et al., "DNA Flexibility Studied by Covalent Closure of Short Fragments Into Circles", Proceedings of The National Academy of Sciences, vol. 78, Issue 8, Aug. 1981, pp. 4833-4837.
Shore et al., "Energetics of DNA Twisting *: I. Relation Between Twist and Cyclization Probability", Journal of Molecular Biology, vol. 170, Issue 4, Nov. 15, 1983, pp. 957-981.
Wang et al., "Balanced-PCR Amplification Allows Unbiased Identification of Genomic Copy Changes in Minute Cell and Tissue Samples", Nucleic Acids Research, vol. 32, 2004.
Kuhn et al., "Template-Independent Ligation of Single-Stranded DNA by T4 DNA Ligase", FEBS Journal 272 (2005) pp. 5991-6000.
Blondal et al., "Isolation and Characterization of a Thermostable RNA Ligase 1 from a Thermus Scotoductus Bacteriophage TS2126 with Good Single-Stranded DNA Ligation Properties", Nucleic Acids Research, 2005, vol. 33, No. 1 135-142.
Li et al., "Whole Genome Amplification of Plasma-Circulating DNA Enables Expanded Screening for Allelic Imbalance in Plasma", The Journal of Molecular Diagnostics, vol. 8, 2006, pp. 22-30.
Nunez et al., "Application of Circular Ligase to Provide Template for Rolling Circle Amplification of Low Amounts of Fragmented DNA", The Nineteenth International Symposium on Human Identification, 2008, 7 pages.
Torchia et al., "Archaeal RNA Ligase is a Homodimeric Protein that Catalyzes Intramolecular Ligation of Single-Stranded RNA and DNA", Nucleic Acids Research, vol. 36, Issue 19, Oct. 2008, pp. 6218-6227.
Beck et al., "Profile of the Circulating DNA in Apparently Healthy Individuals", Clinical Chemistry, vol. 55, Issue 4, Apr. 2009, pp. 730-738.(2009); 13Pages.
Shuman, "DNA Ligases: Progress and Prospects", The Journal of Biological Chemistry, vol. 284, No. 26, Jun. 26, 2009., pp. 17365-17369.
"CircLigase™ II ssDNA Ligase", Cat. Nos. CL9021K and CL9025K, Epicentre, 2011, 5 pages.
Kuo et al., "Amorphization Behavior of Ni57Zr20Ti22Ge1 Powders by Mechanical Alloying", Key Engineering Materials vol. 479 (2011) pp. 48-53.
Tate, et al., "Evaluation of Circular DNA Substrates for Whole Genome Amplification Prior to Forensic Analysis", Forensic Science International: Genetics 6 (2012), pp. 185-190.
Zhelkovsky et al., "Structure-function analysis of Methanobacterium thermoautotrophicum RNA ligase—engineering a thermostable ATP independent enzyme", Zhelkovsky and McReynolds BMC Molecular Biology 2012, 10 pages.

* cited by examiner

*Primary Examiner* — Cynthia B Wilder
(74) *Attorney, Agent, or Firm* — Jenifer E. Haeckl

(57) ABSTRACT

Provided herein are methods for generation and amplification of a single-stranded DNA circle in a single reaction vessel from a linear DNA without any intervening purification steps. The single-stranded DNA circle is generated via a template-independent single-stranded DNA ligation. Whole-genome amplification of circulating nucleic acids extracted from blood is provided. Kits for performing the disclosed methods are also provided.

34 Claims, 14 Drawing Sheets

| Locus | Amplicon size (bp) | Genomic DNA | Plasma DNA | CircLigase II - treated plasma DNA |
|---|---|---|---|---|
| mini CSF1PO | 89-129 | 22.26 | X | 25.55 |
| mini TH01 | 51-98 | 23.43 | X | 25.24 |
| mini TPOX | 65-101 | 24.62 | X | 23.92 |
| mini vWA | 88-148 | 21.29 | X | 20.66 |
| mini D5S818 | 81-117 | 22.14 | X | 26.19 |
| mini D7S820 | 136-176 | 23.46 | X | 27.11 |
| mini D8S1129 | 86-134 | 22.72 | X | 20.26 |
| mini D13S317 | 88-132 | 23.03 | 28.73 | 25.24 |
| mini D16S539 | 88-121 | 20.74 | 20.40 | 20.83 |
| mini D18S51 | 113-193 | 23.84 | X | X |
| Amelogenin | 106, 112 | 20.72 | 29.67 | 22.27 |
| D3S1358 | 99-147 | 20.13 | 20.77 | 20.85 |
| Total | | 12/12 loci | 4/12 loci | 11/12 loci |

FIG. 5

LIGASE-ASSISTED NUCLEIC ACID CIRCULARIZATION AND AMPLIFICATION

FIELD OF INVENTION

The invention generally relates to nucleic acid assays that involve the generation of a single-stranded DNA circle from a single-stranded or double-stranded linear DNA via template-independent single-stranded DNA ligation. It further relates to the amplification and/or detection of the single-stranded DNA circle via rolling circle amplification. Generation of single-stranded DNA circles and subsequent DNA amplification are performed in a single reaction vessel without any intervening isolation and/or purification steps. Kits for performing the methods are also provided.

BACKGROUND

DNA amplification is a process of replicating a target double-stranded DNA (dsDNA) to generate multiple copies of it. Since individual strands of a dsDNA are antiparallel and complementary, each strand may serve as a template strand for the production of its complementary strand. The template strand is preserved as a whole or as a truncated portion and the complementary strand is assembled from deoxynucleoside triphosphates (dNTPs) by a DNA polymerase. The complementary strand synthesis proceeds in 5'→3' direction starting from the 3' terminal end of a primer sequence that is hybridized to the template strand.

Whole-genome amplification (WGA) involves non-specific amplification of a target DNA. WGA is often achieved by multiple displacement amplification (MDA) techniques employing random oligonucleotide primers for priming the DNA synthesis at multiple locations of the target DNA along with a high fidelity DNA polymerase having a strand displacing activity (e.g., Phi29 polymerase). Even though currently available commercial WGA systems such as GenomiPhi (GE Healthcare, USA) and RepliG (Qiagen) kits provide optimal results with high molecular weight target DNA, performance of these systems is poor when the target DNA is short and/or highly fragmented. When the target DNA is fragmented and the sequence length is less than about 1000 nucleotides, amplification of the target DNA using conventional methods results in decreased amplification speed, significant sequence dropout especially near the ends of the target DNA, and highly sequence-biased amplification. As the length of the template DNA is decreased, the likelihood of that strand being primed multiple times decreases in the MDA reaction. This decreases the amplification potential of these shorter fragments. Efficient methods for non-specifically amplifying short, fragmented DNA are therefore highly desirable.

Ligation-mediated polymerase chain reaction (PCR) has been used to amplify fragmented dsDNA. However, only a small fraction of the fragmented DNA gets amplified in these reactions leading to inadequate genome coverage. To efficiently amplify fragmented, target dsDNA, they may first be repaired and then be concatamerized by blunt-end ligation to generate sequences that are longer than 1000 base pairs (bp). However, a relatively higher concentration of the target DNA is often required to promote concatamerization and subsequent amplification. Circularization of double-stranded target DNA has also been employed in various nucleic acid based assays including MDA, WGA, hyper-branched rolling circle amplification (RCA) and massively parallel DNA sequencing. To effectively circularize and amplify fragmented dsDNA, the double-stranded ends of the fragmented DNA are first repaired, followed by blunt-end ligation to form double-stranded DNA circles. However, it is difficult to circularize double-stranded DNA fragments that are less than 500 bp in length.

The double-stranded DNA may be denatured to produce single-stranded DNA (ssDNA), which may further be circularized in a template-dependent intra-molecular ligation reaction using a ligase. However, prior sequence information of the target DNA is required to perform a template-dependent circularization. Template-independent intra-molecular ligation of ssDNA has also been documented. For example, TS2126 RNA ligase (commercially available under the trademarks THERMOPHAGE™ RNA ligase II or THERMOPHAGE™ ssDNA ligase (Prokaria, Matis, Iceland) or CIRCLIGASE™ ssDNA ligase (Epicenter Biotechnologies, Wisconsin, USA) has been used for making digital DNA balls, and/or locus-specific cleavage and amplification of DNA, such as genomic DNA. CIRCLIGASE I™ has a low degree (about 30%) of adenylation where as CIRCLIGASE II™ comprises a substantially adenylated form of TS2126 RNA ligase. Linear, single-stranded complementary DNA (cDNA) molecules prepared from 5'-end fragments of mRNA have also been amplified via rolling circle replication after circularization using TS2126 RNA ligase. By appropriately incorporating a sense RNA polymerase promoter sequence in to the cDNA, the circularized cDNA template has shown to act as a transcription substrate and thus effect the amplification of the mRNA molecules in a biological sample. Further, the TS2126 RNA ligase has been used for amplifying the cDNA ends for random amplification of cDNA ends (RACE). From limited amounts of fragmented DNA, DNA template for rolling circle amplification has also been generated by employing TS2126 RNA ligase. The method involved denaturing the linear, fragmented dsDNA to obtain linear ssDNA fragments, ligating the linear ssDNA with CIRCLIGASE™ ssDNA ligase to obtain single-stranded DNA circle, and then amplifying the single-stranded DNA circle using random primers and Phi29 DNA polymerase via RCA. However, even after optimizing the reaction conditions, the amount of generated single-stranded circular DNA was highly variable and sequence dependent. For example, oligonucleotides comprising a 5'G and a 3'T nucleotide ligated significantly better than its complementary oligonucleotide comprising a 5'A and a 3'C under identical ligation conditions. Further, intra-molecular ligation efficiency varied among linear ssDNA sequences having identical or very similar sizes but with small differences in nucleotide sequence. The efficiency also varied among linear ssDNA sequences of different sizes (e.g., sequence length ranging from 100 bases to kilobases in size). Moreover, all attempts of ligation-amplification reactions involved intermediate isolation, purification and/or cleaning steps, thus making the ligation-amplification workflow cumbersome. For example, analysis of forensic samples of fragmented DNA by circularization followed by rolling circle amplification was carried out in multiple steps comprising 5' DNA phosphorylation, adapter ligation, DNA circularization, and whole-genome amplification. Each step reactions were subjected to a reaction clean-up before performing the next step. No amplification advantage was observed when ligation and amplification was performed in single reaction vessel. However, the multi-step process often resulted in the loss of template DNA and led to failed analysis. Efficient methods for non-specifically amplifying short DNA sequences in a single reaction vessel without any sequence bias and any intervening cleaning steps are therefore highly desirable.

BRIEF DESCRIPTION

In some embodiments, a method for generating a single-stranded DNA circle from a linear DNA is provided. The method comprises the steps of providing a linear DNA, end-repairing the linear DNA by incubating it with a polynucleotide kinase in the presence of a phosphate donor to generate a ligatable DNA sequence having a phosphate group at a 5' terminal end and a hydroxyl group at a 3' terminal end, and performing an intra-molecular ligation of the repaired, ligatable DNA sequence with a ligase in order to generate the single-stranded DNA circle. All steps of the method are performed in single reaction vessel without any intervening isolation or purification steps. The phosphate donor may be a guanosine triphosphate (GTP), a cytidine triphosphate (CTP), a uridine triphosphate (UTP), a deoxythymidine triphosphate (dTTP) or a combination thereof. The linear DNA may either be double-stranded or single-stranded DNA. DNA may be a fragmented DNA such as circulating DNA. The ligatable DNA, if in double-stranded form, needs to be denatured prior to intra-molecular ligation reaction. A pre-adenylated ligase that is capable of template-independent, intra-molecular ligation of single-stranded DNA sequences may be employed for the ligation reaction.

In some embodiments, a method for generating a single-stranded DNA circle from a linear DNA is provided, wherein the method employs a DNA pre-adenylation step prior to an intra-molecular ligation step. The linear DNA may optionally be incubated with a polynucleotide kinase in the presence of adenosine triphosphate (ATP) to generate a ligatable DNA sequence that comprises a phosphate group at a 5' terminal end and a hydroxyl group at a 3' terminal end. Generation of ligatable DNA sequence from the linear DNA may be preferred if the linear DNA is in a highly fragmented form. The linear DNA or the ligatable DNA sequence is then incubated with an adenylating enzyme in presence of ATP to generate a 5' adenylated DNA sequence. The 5' adenylated DNA sequence is then incubated with a non-adenylated ligase, which is capable of template-independent intra-molecular ligation of the 5' adenylated DNA sequence to generate the single-stranded DNA circle. All steps of the method are performed in a single reaction vessel without any intervening isolation or purification steps. ATP may have to be removed from the reaction mixture (e.g., by treating the reaction mixture with a phosphatase) before the intra-molecular ligation reaction if the non-adenylated ligase is an ATP-dependent ligase. If the 5' adenylated DNA is in double-stranded form, it needs to be denatured prior to the intra-molecular ligation reaction.

DRAWINGS

These and other features, aspects and advantages of the invention will become better understood when the following detailed description is read with reference to the accompanying figures.

FIG. 5 illustrates the effectiveness of ligase-assisted whole-genome amplification for sensitive and balanced DNA amplification of twelve different CODIS loci.

DETAILED DESCRIPTION

Figure 1:
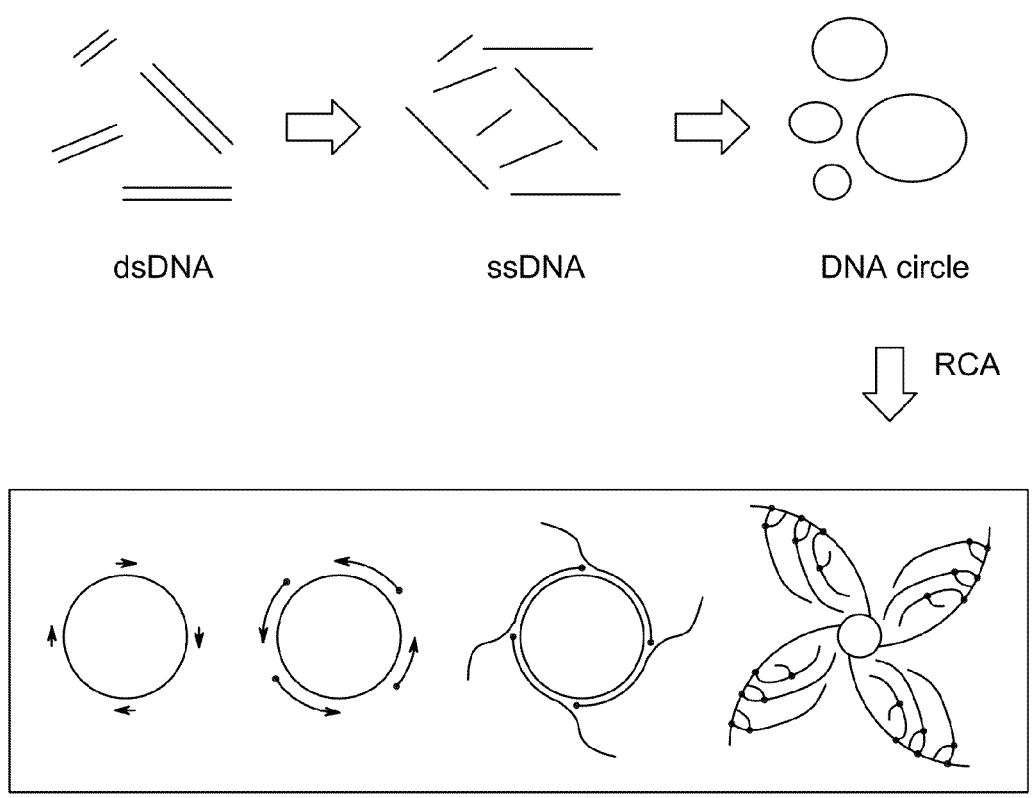
FIG. 1 illustrates a schematic representation of an embodiment of a ligase-assisted whole-genome amplification of a fragmented dsDNA.

The following detailed description is exemplary and not intended to limit the invention or uses of the invention. Throughout the specification, exemplification of specific terms should be considered as non-limiting examples. The singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Where necessary, ranges have been supplied, and those ranges are inclusive of all sub-ranges there between. To more clearly and concisely describe and point out the subject matter of the claimed invention, the following definitions are provided for specific terms, which are used in the following description and the appended claims.

As used herein, the term "nucleoside" refers to a glycosylamine compound wherein a nucleic acid base (nucleobase) is linked to a sugar moiety. A "nucleotide" refers to a nucleoside phosphate. A nucleotide may be represented using alphabetical letters (letter designation) corresponding to its nucleoside as described in Table 1. For example, A denotes adenosine (a nucleoside containing the nucleobase, adenine), C denotes cytidine, G denotes guanosine, U denotes uridine, and T denotes thymidine (5-methyl uridine). W denotes either A or T/U, and S denotes either G or C. N represents a random nucleoside and dNTP refers to deoxyribonucleoside triphosphate. N may be any of A, C, G, or T/U.

TABLE 1

Letter designations of various nucleotides.

| Symbol Letter | Nucleotide represented by the symbol Letter |
|---|---|
| G | G |
| A | A |
| T | T |
| C | C |
| U | U |
| R | G or A |
| Y | T/U or C |
| M | A or C |
| K | G or T/U |
| S | G or C |
| W | A or T/U |
| H | A or C or T/U |
| B | G or T/U or C |
| V | G or C or A |
| D | G or A or T/U |
| N | G or A or T/U or C |

As used herein, the term "nucleotide analogue" refers to compounds that are structurally analogous to naturally occurring nucleotides. The nucleotide analogue may have an altered phosphate backbone, sugar moiety, nucleobase, or combinations thereof. Nucleotide analogues may be a natural nucleotide, a synthetic nucleotide, a modified nucleotide, or a surrogate replacement moiety (e.g., inosine). Generally, nucleotide analogues with altered nucleobases confer, among other things, different base pairing and base stacking proprieties. As used herein, the term "LNA (Locked Nucleic Acid) nucleotide" refers to a nucleotide analogue, wherein the sugar moiety of the nucleotide contains a bicyclic furanose unit locked in a ribonucleic acid (RNA)-mimicking sugar conformation. The structural change from a deoxyribonucleotide (or a ribonucleotide) to the LNA nucleotide is limited from a chemical perspective, namely the introduction of an additional linkage between carbon atoms at 2' position and 4' position (e.g., 2'-C, 4'-C-oxymethylene linkage; see, for example, Singh, S. K., et. al., Chem. Comm, 4, 455-456, 1998, or Koshkin, A. A., et. al., Tetrahedron, 54, 3607-3630, 1998.)). The 2' and 4' position of the furanose unit in the LNA nucleotide may be linked by an O-methylene (e.g., oxy-LNA: 2'-O, 4'-C-methylene-β-D-ribofuranosyl nucleotide), a S-methylene (thio-LNA), or a NH-methylene moiety (amino-LNA), and the like. Such linkages restrict the conformational freedom of the furanose ring. LNA oligonucleotides display enhanced hybridization affinity toward complementary single-stranded RNA, and complementary single- or double-stranded DNA. The LNA oligonucleotides may induce A-type (RNA-like) duplex conformations. Nucleotide analogues having altered phosphate-sugar backbone (e.g., PNA, LNA) often modify, among other things, the chain properties such as secondary structure formation. A star (*) sign preceding a letter designation denotes that the nucleotide designated by the letter is a phosphorothioate modified nucleotide. For example, *N represents a phosphorothioate modified random nucleotide. A plus (+) sign preceding a letter designation denotes that the nucleotide designated by the letter is a LNA nucleotide. For example, +A represents an adenosine LNA nucleotide, and +N represents a locked random nucleotide (i.e., a random LNA nucleotide).

As used herein, the term "oligonucleotide" refers to oligomers of nucleotides. The term "nucleic acid" as used herein refers to polymers of nucleotides. The term "sequence" as used herein refers to a nucleotide sequence of an oligonucleotide or a nucleic acid. Throughout the specification, whenever an oligonucleotide or nucleic acid is represented by a sequence of letters, the nucleotides are in 5'→3'→ order from left to right. For example, an oligonucleotide represented by a letter sequence $(W)_x(N)_y(S)_z$, wherein x=2, y=3 and z=1, represents an oligonucleotide sequence WWNNNS, wherein W is the 5' terminal nucleotide and S is the 3' terminal nucleotide. The oligonucleotides or nucleic acids may be a DNA, an RNA, or their analogues (e.g., phosphorothioate analogue). The oligonucleotides or nucleic acids may also include modified bases and/or backbones (e.g., modified phosphate linkage or modified sugar moiety). Non-limiting examples of synthetic backbones that confer stability and/or other advantages to the nucleic acids may include phosphorothioate linkages, peptide nucleic acid, locked nucleic acid, xylose nucleic acid, or analogues thereof.

As used herein, the term "primer" refers to a short linear oligonucleotide that hybridizes to a target nucleic acid sequence (e.g., a DNA template to be amplified) to prime a nucleic acid synthesis reaction. The primer may be an RNA oligonucleotide, a DNA oligonucleotide, or a chimeric sequence. The primer may contain natural, synthetic, or modified nucleotides. Both the upper and lower limits of the length of the primer are empirically determined. The lower limit on primer length is the minimum length that is required to form a stable duplex upon hybridization with the target nucleic acid under nucleic acid amplification reaction conditions. Very short primers (usually less than 3 nucleotides long) do not form thermodynamically stable duplexes with target nucleic acid under such hybridization conditions. The upper limit is often determined by the possibility of having a duplex formation in a region other than the pre-determined nucleic acid sequence in the target nucleic acid. Generally, suitable primer lengths are in the range of about 3 nucleotides long to about 40 nucleotides long.

As used herein, the term "random primer" refers to a mixture of primer sequences, generated by randomizing a nucleotide at any given location in an oligonucleotide sequence in such a way that the given location may consist of any of the possible nucleotides or their analogues (complete randomization). Thus the random primer is a random mixture of oligonucleotide sequences, consisting of every possible combination of nucleotides within the sequence. For example, a hexamer random primer may be represented by a sequence NNNNNN or $(N)_6$. A hexamer random DNA primer consists of every possible hexamer combinations of 4 DNA nucleotides, A, C, G and T, resulting in a random mixture comprising $4^6$ (4,096) unique hexamer DNA oligonucleotide sequences. Random primers may be effectively used to prime a nucleic acid synthesis reaction when the target nucleic acid's sequence is unknown or for whole-genome amplification reaction.

As described herein, the term "partially constrained primer" refers to a mixture of primer sequences, generated by completely randomizing some of the nucleotides of an oligonucleotide sequence (i.e., the nucleotide may be any of A, T/U, C, G, or their analogues) while restricting the complete randomization of some other nucleotides (i.e., the randomization of nucleotides at certain locations are to a lesser extent than the possible combinations A, T/U, C, G, or their analogues). For example, a partially constrained DNA hexamer primer represented by WNNNNN, represents a mixture of primer sequences wherein the 5' terminal nucleotide of all the sequences in the mixture is either A or T. Here, the 5' terminal nucleotide is constrained to two possible combinations (A or T) in contrast to the maximum four possible combinations (A, T, G or C) of a completely random DNA primer (NNNNNN). Suitable primer lengths of a partially constrained primer may be in the range of about 3 nucleotides long to about 15 nucleotides long.

As described herein, the term "partially constrained primer having a terminal mismatch primer-dimer structure" refers to a partially constrained primer sequence, wherein when two individual primer sequences in the partially constrained primer hybridize each other inter-molecularly, with an internal homology of three or more nucleotides, to form a primer-dimer structure having no recessed ends, or a primer-dimer structure having a single-nucleotide base 3' recessed ends, or a primer-dimer structure having a two-nucleotide base 3' recessed ends, there exists a nucleotide mismatch (i.e., nucleotides do not base-pair) at both the 3' terminal nucleotides in the primer-dimer structure. For example, a partially constrained pentamer primer represented by WNNNS provides a terminal mismatch at both the 3' terminal nucleotides when it is inter-molecularly hybridized to form a primer-dimer structure having no recessed ends. In the primer-dimer structure, there exists an internal homology of three nucleotides (i.e., the three random nucleotides in WNNNS may base-pair with each other when the primer-dimer structure having no recessed ends is formed by inter-molecular hybridization). However, this primer example does not provide a terminal mismatch when it is inter-molecularly hybridized to form a primer-dimer structure with single-nucleotide base 3' recessed ends. Similarly, a partially constrained hexamer primer represented by WWNNNS provides a terminal mismatch at both the 3' terminal nucleotides when it is inter-molecularly hybridized to form a primer-dimer structure having no recessed ends. Moreover, this primer example provides a terminal mismatch at both the 3' terminal nucleotides even when it is inter-molecularly hybridized to form a primer-dimer structure having a single-nucleotide base 3' recessed ends. A partially constrained heptamer primer represented by WWWNNNS provides a terminal mismatch at both the 3' terminal nucleotides when it is inter-molecularly hybridized to form a primer-dimer structure having no recessed ends. Further, this primer example provides a terminal mismatch at both the 3' terminal nucleotides when it is inter-molecularly hybridized to form a primer-dimer structure having a single-nucleotide base 3' recessed ends, or to form a primer-dimer structure having a two-nucleotide base 3' recessed ends.

As used herein, the term "rolling circle amplification (RCA)" refers to a nucleic acid amplification reaction that amplifies a circular nucleic acid template (e.g., single stranded DNA circles) via a rolling circle mechanism. Rolling circle amplification reaction is initiated by the hybridization of a primer to a circular, often single-stranded, nucleic acid template. The nucleic acid polymerase then extends the primer that is hybridized to the circular nucleic acid template by continuously progressing around the circular nucleic acid template to replicate the sequence of the nucleic acid template over and over again (rolling circle mechanism). The rolling circle amplification typically produces concatamers comprising tandem repeat units of the circular nucleic acid template sequence. The rolling circle amplification may be a linear RCA (LRCA), exhibiting linear amplification kinetics (e.g., RCA using a single specific primer), or may be an exponential RCA (ERCA) exhibiting exponential amplification kinetics. Rolling circle amplification may also be performed using multiple primers (multiply primed rolling circle amplification or MPRCA) leading to hyper-branched concatamers. For example, in a double-primed RCA, one primer may be complementary, as in the linear RCA, to the circular nucleic acid template, whereas the other may be complementary to the tandem repeat unit nucleic acid sequences of the RCA product. Consequently, the double-primed RCA may proceed as a chain reaction with exponential (geometric) amplification kinetics featuring a ramifying cascade of multiple-hybridization, primer-extension, and strand-displacement events involving both the primers. This often generates a discrete set of concatemeric, double-stranded nucleic acid amplification products. The rolling circle amplification may be performed in-vitro under isothermal conditions using a suitable nucleic acid polymerase such as Phi29 DNA polymerase.

As used herein, multiple displacement amplification (MDA) refers to a nucleic acid amplification method, wherein the amplification involves the steps of annealing a primer to a denatured nucleic acid followed by a strand displacement nucleic acid synthesis. As nucleic acid is synthesized by strand displacement, a gradually increasing number of priming events occur, forming a network of hyper-branched nucleic acid structures. MDA is highly useful for whole-genome amplification for generating high-molecular weight DNA with limited sequence bias from a small amount of genomic DNA sample. Any strand displacing nucleic acid polymerase that has a strand displacement activity apart from its nucleic acid synthesis activity such as a Phi29 DNA polymerase or a large fragment of the Bst DNA polymerase may be used in MDA. MDA is often performed under isothermal reaction conditions, using random primers for achieving amplification with limited sequence bias.

As used herein, the term "pre-adenylated ligase" refers to a ligase that is in its adenylated form. The adenylated form of a ligase is capable of intra-molecular ligation of a linear, ssDNA molecule having a 5' phosphoryl group and a 3' hydroxyl group in the absence of ATP or dATP. A ligation using a pre-adenylated ligase refers to a ligation reaction wherein a high proportion of the ligase molecules that are used in the reaction are in their adenylated form. Generally more than 60% of the ligase molecules may be in their adenylated form. In some embodiments, when a ligation reaction is performed using a pre-adenylated ligase, more than 70% of the ligase molecules employed for the reaction may be in their adenylated form. In some other embodiments, when a ligation reaction is performed using a pre-adenylated ligase, more than 80%, 90%, or 95% of the ligase molecules employed for the reaction may be in their adenylated form.

As used herein the term "adenylating enzyme" refers to an enzyme that is capable of adenylating a nucleic sequence to generate a 5' adenylated nucleic acid. The 5'adenylated nucleic acid as used herein refers to a nucleic acid sequence that has a hydroxyl group at its 3' end and has adenylated terminal nucleotide at its 5' end. For example, a 5' adenylated DNA (AppDNA), refers to a DNA sequence that is adenylated at its 5' end and has a hydroxyl group at its 3' end.

As used herein the term "non-adenylated ligase" refers to a ligase that is in their non-adenylated form. The non-adenylated form of the ligase is capable of intra-molecular ligation of a linear, 5'-adenylated ssDNA molecule having a 3' hydroxyl group in the absence of ATP or dATP. A ligation using a non-adenylated ligase refers to a ligation reaction wherein a high proportion of the ligase molecules that are used in the reaction are in their non-adenylated form. Generally more than 60% of the ligase molecules may be in their non-adenylated form. In some embodiments, when a ligation reaction is performed using a non-adenylated ligase, more than 70% of the ligase molecules employed for the reaction may be in their un-adenylated form. In some other embodiments, when a ligation reaction is performed using a non-adenylated ligase, more than 80%, 90% or 95% of the ligase molecules employed for the reaction may be in their un-adenylated form.

In some embodiments, a method for generating a single-stranded DNA circle from a linear DNA is provided. The linear DNA may be a fragmented, linear DNA. The fragmented DNA may be a circulating DNA, an ancient DNA or a DNA degraded by environmental exposure, or a formalin-fixed DNA. The length of a fragmented, linear DNA may range from 15 nucleotides to 21000 nucleotides. The fragmented, linear DNA may comprise sequences that have non-ligatable terminal ends. For example, the linear DNA may have either a 5' hydroxyl group or a 3' phosphoryl group or both. In some embodiments, the method comprises the steps of providing a linear DNA, end-repairing the linear DNA by incubating it with a polynucleotide kinase (PNK) in the presence of a phosphate donor to generate a ligatable DNA sequence having a phosphate group at a 5' terminal end and a hydroxyl group at a 3' terminal end, and performing an intra-molecular ligation of the ligatable DNA sequence with a ligase to generate the single-stranded DNA circle. End repair may include phosphorylation of a 5' terminal nucleotide, de-phosphorylation of a 3' terminal nucleotide or both to generate a ligatable DNA sequence. The end-repaired, ligatable DNA, if in double-stranded form, needs to be denatured prior to the intra-molecular ligation reaction. In some embodiments, DNA is denatured prior to PNK reaction. Phosphorylation or dephosphorylation of single-stranded DNA is generally more efficient than that of a double-stranded blunt or 5'-recessed ends. The phosphate donor and its concentration in the reaction mixture are selected such that it does not inhibit the subsequent intra-molecular ligation reaction. For example, any suitable phosphate donor other than adenosine triphosphate (ATP) or deoxyadenosine triphosphate (dATP) may be used for the end-repair reaction using PNK. Suitable phosphate donors include, but are not limited to, guanosine triphosphate (GTP), cytidine triphosphate (CTP), uridine triphosphate (UTP) or dexoythymine triphosphate (dTTP). In some embodiments, a pre-adenylated ligase is used for the ligation reaction. Any pre-adenylated ligase that is capable of template-independent, single-stranded DNA sequences may be employed. In some embodiments, a substantially adenylated form of TS2126 RNA ligase is used for the template-independent, intra-molecular ligation reaction. The kinase reaction and the ligation reaction are performed in the absence of ATP and/or dATP. All the steps of the method are performed in single reaction vessel without any intervening isolation or purification steps. The individual steps of the methods may be performed simultaneously or in sequential manner without any intermediate purification or isolation steps. For example, PNK along with GTP may be added to a reaction vessel (e.g., eppendorf tube) containing a nucleic acid solution comprising the linear target DNA to facilitate the end-repair of the linear target DNA. Any PNK that has a 5' phosphorylation and a 3' phosphatase activity (e.g., T4 PNK) may be used for the end-repair reaction. A combination of PNKs each of which has 5' phosphorylation or a 3' phosphatase may also be used for the end-repair reaction. Once the kinase reaction is completed, a pre-adenylated ligase may be added to the same reaction vessel to facilitate the intra-molecular ligation reaction.

The linear DNA may be a double-stranded or single-stranded DNA of either natural or synthetic origin. The DNA may be obtained from a biological sample (e.g., a sample obtained from a biological subject) or discovered from unknown objects (e.g., DNA obtained during a forensic investigation) in vivo or in vitro. For example, it may be obtained from, but not limited to, bodily fluid (e.g., blood, blood plasma, serum, urine, milk, cerebrospinal fluid, pleural fluid, lymph, tear, sputum, saliva, stool, lung aspirate, throat or genital swabs), organs, tissues, cell cultures, cell fractions, sections (e.g., sectional portions of an organ or tissue) or cells isolated from the biological subject or from a particular region (e.g., a region containing diseased cells, or circulating tumor cells) of the biological subject. The biological sample that contains or suspected to contain the target linear DNA (i.e., linear DNA of interest) may be of eukaryotic origin, prokaryotic origin, viral origin or bacteriophage origin. For example, the target linear DNA may be obtained from an insect, a protozoa, a bird, a fish, a reptile, a mammal (e.g., rat, mouse, cow, dog, guinea pig, or rabbit), or a primate (e.g., chimpanzee or human). The linear DNA may be a genomic DNA or a cDNA (complementary DNA). The cDNA may be generated from an RNA template (e.g., mRNA, ribosomal RNA) using a reverse transcriptase enzyme. The linear DNA may be a fragmented DNA and may have non-ligatable terminal nucleotides. For example, linear DNA may comprise a 5' hydroxyl group and/or a 3' phosphate group such that a DNA ligase cannot perform an intra-molecular ligation reaction. The linear DNA may be dispersed in solution or may be immobilized on a solid support, such as in blots, assays, arrays, glass slides, microtiter plates or ELISA plates. For example, the linear DNA may be immobilized on a substrate through a primer and then may be circularized and amplified.

When the linear DNA is in a double-stranded form, it needs be denatured to a single-stranded form prior to the intra-molecular ligation reaction. This may be achieved by using any of the art-recognized methods for the conversion of dsDNA to ssDNA sequences. For example, the dsDNA may be thermally denatured, chemically denatured, or both thermally and chemically denatured. The dsDNA may be chemically denatured using a denaturant (e.g., glycerol, ethylene glycol, formamide, urea or a combination thereof) that reduces the melting temperature of dsDNA. The denaturant may reduce the melting temperature by 5° C. to 6° C. for every 10% (vol./vol.) of the denaturant added to the reaction mixture. The denaturant or combination of denaturants (e.g., 10% glycerol and 6-7% ethylene glycol) may comprise 1%, 5%, 10%, 15%, 20%, or 25% of reaction mixture (vol./vol.). Salts that reduce hybridization stringency may be included in the reaction buffers at low concentrations to chemically denature the dsDNA at low temperatures. The dsDNA may be thermally denatured by heating the dsDNA, for example, at 95° C.

After the denaturing step, the generated ssDNA may be treated with a DNA or RNA ligase that is capable of intra-molecular ligation of ssDNA substrates in the absence of a template to form the single-stranded DNA circles. Suitable ligases that may be used for the ligation reaction include, but are not limited to, TS2126 RNA ligase, T4 DNA ligase, T3 DNA ligase or E. coli DNA ligase. The conversion of linear, single-stranded DNA molecules to single-stranded DNA circles is conventionally performed via a template-dependent intra-molecular ligation reaction using a ligation enzyme such as T4 RNA ligase. However, template-dependent intra-molecular ligation of single-stranded DNA or single-stranded RNA has met only with limited success, particularly when the circularization of ssDNA molecules is to be performed in a population of ssDNA molecules of unknown sequence and/or size. Even though bacteriophage T4 RNA ligase I exhibits a template-independent intra-molecular ligation activity, this activity is far too low and inefficient for practical use in generating circular ssDNA molecules from linear ssDNA molecules.

In some embodiments, conversion of the ssDNA to single-stranded DNA circle is performed with a thermostable RNA ligase that has good template-independent, intra-molecular ligation activity for linear ssDNA and/or ssRNA substrates that have 5' phosphoryl and 3' hydroxyl groups. The ligase may be in a substantially pre-adenylated form. For example, TS2126 RNA ligase derived from the *Thermus* bacteriophage TS2126 that infects the thermophilic bacterium, *Thermus scotoductus* may be employed for template-independent circularization of the fragmented linear ssDNA to circular ssDNA. TS2126 RNA ligase is more thermostable (stable up to about 75° C.) than many of the mesophilic RNA ligases such as the T4 RNA ligase. The range of temperature for TS2126 RNA ligase activity can be greater than about 40° C., for example, from about 50° C. to about 75° C. Due to this, TS2126 RNA ligase may be used at higher temperatures, which further reduce undesirable secondary structures of ssDNA. The circularization of linear ssDNA may also be achieved by a ligase other than TS2126 RNA ligase or by employing any other enzyme having DNA joining activity such as topoisomerase. In some embodiments, the circularization of fragmented, single stranded DNA molecule is achieved by an RNA ligase 1 derived from thermophilic archeabacteria, *Methanobacterium thermoautotrophicum* (Mth RNA ligase) that has high template-independent ligase activity in circularizing linear, fragmented ssDNA molecules.

In some embodiments, a method for improving the efficiency of circularization of ssDNA by TS2126 RNA ligase is provided. Use of HEPES buffer having a pH of 8.0 for the ligation reaction increased the ligation efficiency. Template-independent ssDNA ligation was inefficient when the reaction was performed in TRIS buffer (e.g., For CIRCLIGASE II™, the suggested 10× reaction buffer by EpiCenter comprises 0.33 M TRIS-Acetate (pH 7.5), 0.66 M potassium acetate, and 5 mM DTT). Further, manganese, an essential co-factor for the ligation reaction, is rapidly oxidized under alkaline conditions and forms a precipitate in the presence of TRIS. Air oxidation of $Mn^{2+}$ to $Mn^{3+}$ may be facilitated by the anions that can strongly complex the $Mn^{3+}$ ions. For example, when equal volumes of 0.2 mol/liter Tris with pH appropriately adjusted with HCl and 2 mmol/liter $MnCl_2$ were mixed, the color change was immediate at pH 9.3 (the pH of TRIS base alone); had an initial time lag of about 3 minutes at pH 8.5; and was not detectable in 1 hour at pH values below 8.3. Although the reaction did not occur at lower pH, the changes observed at higher pH were not reversed by adding acid. Due to rapid oxidation of manganese in TRIS buffer, a higher concentration of manganese is essential for the ligation reaction (e.g., addition of $MnCl_2$ to a final concentration of 2.5 mM) when the intra-molecular ligation is performed in TRIS buffer. Further, it becomes difficult to accurately predict the working concentration of manganese in the reaction as the manganese concentration continues to decrease over time. Higher concentrations of manganese may lead to higher error-rate of the polymerase during amplification when the ligation and amplification is performed in a single reaction vessel. By substituting TRIS buffer with HEPES buffer in the ligation reaction, effective intra-molecular ligation may be achieved with manganese ion concentration less than 0.5 mM. Apart from HEPES, any of other the Good's buffers (see, for example, Good, Norman et al. Biochemistry, 5 (2): 467-477, 1966; and Good, Norman et al., Methods Enzymol., 24: 53-68, 1972.) may be employed for the intra-molecular ligation reaction.

The ssDNA circles in the ligation reaction mixture may be amplified under isothermal conditions via rolling circle amplification (RCA) methods. The amplification reagents including DNA polymerase, primers and dNTPs may be added to the same reaction vessel to produce an amplification reaction mixture and to initiate an RCA reaction. The amplification reaction mixture may further include reagents such as single-stranded DNA binding proteins and/or suitable amplification reaction buffers. The amplification of ssDNA circles is performed in the same reaction vessel in which ligation is performed. Isolation or purification of the ssDNA circles and/or removal of the ligase is not necessary prior to the amplification reaction. The amplified DNA may be detected by any of the currently known methods for DNA detection.

RCA may be performed by using any of the DNA polymerases that are known in the art such as a Phi29 DNA polymerase. It may be performed using a random primer mixture or by using a specific primer. In some embodiments, random primers are used for the RCA reaction. Primer sequences comprising one or more nucleotide analogues (e.g., LNA nucleotides, 2-Amino-A, or 2-Thio T modification) may also be used. In some embodiments, nuclease-resistant primers (e.g., primer sequences comprising phosphorothioate groups at appropriate positions) are employed for the amplification reactions (e.g., NNNN*N*N). In some embodiments, RCA may be performed by contacting the ssDNA circles with a primer solution comprising a random primer mixture to form a nucleic acid template-primer complex; contacting the nucleic acid template-primer complex with a DNA polymerase and deoxyribonucleoside triphosphates; and amplifying the nucleic acid template. In some embodiments, the primer solution comprises a partially constrained primer such as WWNNS. The partially constrained primer may have a terminally mismatched primer-dimer structure. In some embodiments, a partially constrained primer that consists of a nucleotide sequence $(W)_x(N)_y(S)_z$, wherein x, y and z are integer values independent of each other, and wherein value of x is 2 or 3, value of y is 2, 3 or 4, and value of z is 1 or 2 are used for the RCA reaction. The partially constrained primer may comprise one or more nucleotide analogues. In some embodiments, a nuclease-resistant, partially constrained primer comprising a modified nucleotide, and having terminal mismatch primer-dimer structure is employed for RCA reaction. Suitable primer sequences include, but are not limited to, +W+WNNS, W+W+NNS, +W+WNNNS, W+W+NNNS, W+W+NN*S, +W+WNN*S, W+W+NNN*S, +W+WNNN*S, W+W+N*N*S, +W+WN*N*S, W+W+NN*N*S, or +W+WNN*N*S. In some embodiments, RCA reaction is performed by contacting the ssDNA circle with a primer solution that consists essentially of a partially constrained primer mixture comprising a terminal mismatch primer-dimer structure and amplifying the ssDNA circle. In some other embodiments, RCA reaction is performed by contacting the ssDNA circle with a primer solution that consists essentially of a partially constrained primer mixture comprising a nucleotide analogue and amplifying the ssDNA circle.

RCA of ssDNA circles produces large quantities of DNA with reduced sequence dropout and reduced amplification bias. The entire process of ssDNA ligation and amplification may be performed in a single tube without any intermediate purification or isolation steps.

In some embodiments, methods for amplification of limiting quantities of linear fragmented DNA via multiple displacement amplification (MDA) are provided. Conventional methods of MDA, when attempted on a linear fragmented DNA, result in decreased amplification speed and highly sequence-biased amplification. Moreover, significant sequence dropout is often observed particularly near the ends of the fragmented DNA. To overcome these limitations, the fragmented dsDNA is first converted to ssDNA. The ssDNA is then converted to single-stranded, circular DNA (i.e., DNA circle) via a template-independent intra-molecular ligation reaction, thereby eliminating the problematic DNA ends. Even ssDNA sequences that are shorter than 500 bp may be circularized using template-independent intra-molecular ligation of ssDNA. Further, no prior knowledge of the target sequence is needed to create DNA circles when the ligation of the ssDNA is performed in a template-independent manner. Prior to circularization, fragmented DNA may be treated with a PNK to repair the non-ligatable terminal ends. After circularization of the fragmented ssDNA, MDA is performed on the circularized DNA. The amplification reaction may be performed under isothermal conditions via employing rolling circle amplification (RCA) methods. RCA may be performed using commercially available RCA amplification kits such as TempliPhi™ RCA kit (GE Healthcare). The TempliPhi™ rolling-circle amplification employs locked nucleic acid-containing random primers, which provide higher sensitivity and amplification balance. In some embodiments, nuclease-resistant primers are used for RCA reaction. The methods disclosed herein improve amplification sensitivity, reduce sequence dropout and allow more balanced amplification. Since template-independent circularization of single-stranded fragmented DNA may be achieved on shorter sequences even at lower concentrations, a more balanced DNA amplification with faster kinetics and improved sequence coverage may be achieved when ligase-assisted whole-genome amplification is employed for amplification of highly fragmented DNA (e.g. circulating DNA in blood plasma). For example, the persistence length of ssDNA may be as low as 15 nucleotides for template-independent circularization of ssDNA. When CIRCLIGASE™ is employed for ligation reaction, under standard conditions, virtually no linear concatamers or circular concatmers are produced. Further, both the circularization and amplification reactions may be performed in a single reaction vessel without any intermediated purification or isolation steps thereby reducing the chances of contamination and simplifying the amplification workflow. Ligase-assisted whole-genome amplification methods may be employed for, but not limited to, analyzing circulating plasma DNA, fragmented DNA isolated from formalin fixed paraffin-embedded (FFPE) samples, forensics DNA samples that have been exposed to environmental conditions or ancient DNA samples. The amplified library may further be used for targeted detection of amplified sequences via qPCR or sequencing.

Various ligation-assisted whole-genome amplification methods described herein that comprise prior ligation of ssDNA fragments to DNA circles followed by rolling circle amplification, provide preferential amplification of a fragmented DNA over a high molecular weight genomic DNA. For example, plasma preparations comprising circulating DNA may often be contaminated with genomic DNA that are released from blood cells during the purification process. Conventional methods of whole-genome amplification via MDA amplify both the circulating DNA and the genomic DNA. In contrast, when fragmented, circulating DNA molecules are first circularized with TS2126 RNA followed by amplification of the circularized DNA molecules via RCA employing a Phi29 DNA polymerase the circulating DNA was preferentially amplified over the high molecular weight genomic DNA. Such preferential amplification of fragmented DNA over the genomic DNA is particularly suitable for diagnostic applications since diagnostically relevant DNA may be preferentially amplified for downstream analysis (see, Example 4). Further, ligase-assisted whole-genome amplification allows more robust amplification of fragmented DNA when compared to conventional MDA-based whole-genome amplification.

FIG. 1 depicts a schematic representation of an embodiment of ligase-assisted whole-genome amplification of a fragmented dsDNA. The persistence length of double-stranded DNA is much higher (~150 bp) and its innate stiffness makes circularization of fragments less than 500 bp highly inefficient. Further, with small double-stranded fragmented DNA molecules of about 250 bp range, circularization is inefficient unless the ends are in proper alignment (~10.5 bp/turn). In contrast, the persistence length of the circularization of single-stranded fragmented DNA is very small, approximately 15 nucleotides, when compared to the double-stranded fragmented DNA. As depicted in FIG. 1, in ligase-assisted whole-genome amplification, fragmented dsDNA is first converted into single-stranded DNA circles. This may be achieved by incubating the fragmented double-stranded DNA at 95° C. for a sufficient period to denature the dsDNA into single strands. The fragmented ssDNA is then treated with a DNA or RNA ligase that is capable of template-independent, intra-molecular ligation of single-stranded DNA substrates to generate the single-stranded DNA circles. Non-limiting examples of ligases that may be used for intra-molecular ligation includes, CIRCLIGASE™, T3 DNA ligase, T4 RNA ligase, Mth RNA ligase (MthRnl1), or *E. coli* ligase. Amplification reagents, including DNA polymerase, random primers, and dNTPs are then added to initiate a RCA reaction on the single-stranded DNA circles. This ligase-assisted whole-genome amplification employing RCA produces large quantities of DNA with reduced sequence dropout and amplification bias in contrast to the conventional whole-genome amplification methods. Therefore, it may be used to amplify and detect even highly fragmented DNA. The entire process of generation of the single-stranded DNA circles and its subsequent amplification by RCA is done in a single tube without any intervening purification steps.

Figure 8:
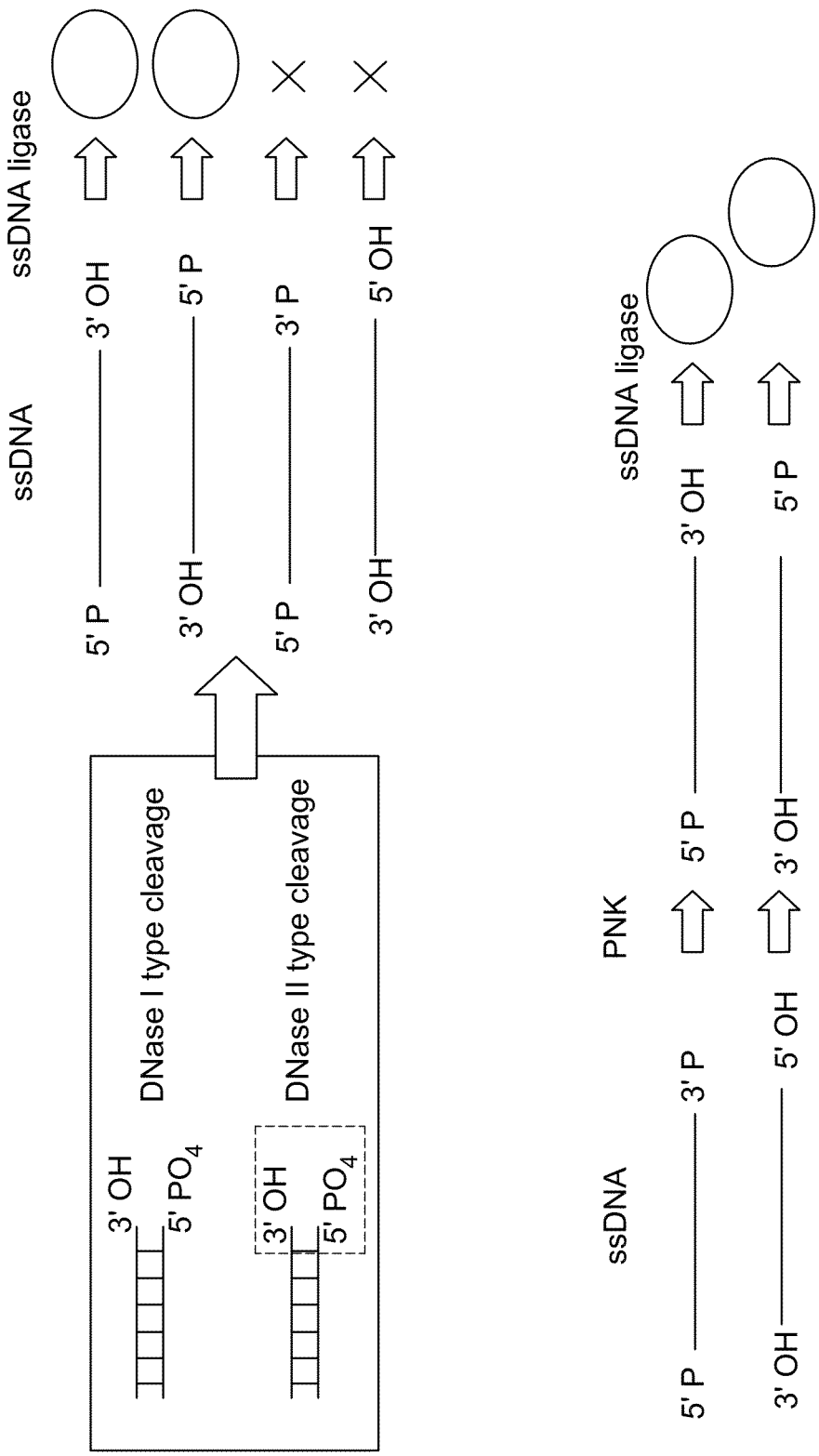
FIG. 8 illustrates a schematic representation of ligase-assisted whole-genome amplification that includes the processing (e.g., end-repair) of a fragmented DNA using a polynucleotide kinase followed by ligase-assisted amplification of the processed fragmented DNA.

In some embodiments, a single-tube workflow is provided for ligase-assisted whole-genome amplification of fragmented DNA that includes processing of a fragmented DNA to repair the non-ligatable DNA ends. For example, if a fragmented single-stranded DNA does not contain a 5' phosphoryl group and a 3' hydroxyl group, it may not get ligated in an intra-molecular ligation reaction. Presence of such non-ligatable DNA sequences may cause an amplification bias in the ligase-assisted whole-genome amplification. For example, as schematically represented FIG. 8., DNA fragments that are generated by DNAse II digestion during cell death may contain a 5' hydroxyl group, a 3' phosphoryl group. The single-stranded DNA fragments originating from such double-stranded DNA fragments that contain a 5' hydroxyl group, a 3' phosphoryl group will not get circularized in an intra-molecular ligation reaction. Thus DNAse II type breaks are likely to be under-represented in whole-genome amplification. In some embodiments, the fragmented DNA is treated with a kinase (e.g., a T4 Polynucleotide Kinase, TPK) to phosphorylate the 5' hydroxyl groups and/or dephosphorylate the 3' phosphoryl group of the fragmented DNA. Inclusion of kinase in the reaction allows efficient circularization of fragments in a pool that do not contain a 5' phosphate. Phosphorylating the 5' ends of the fragmented DNA with a kinase followed by amplification of the fragmented DNA creates a more representative library.

Figure 9:
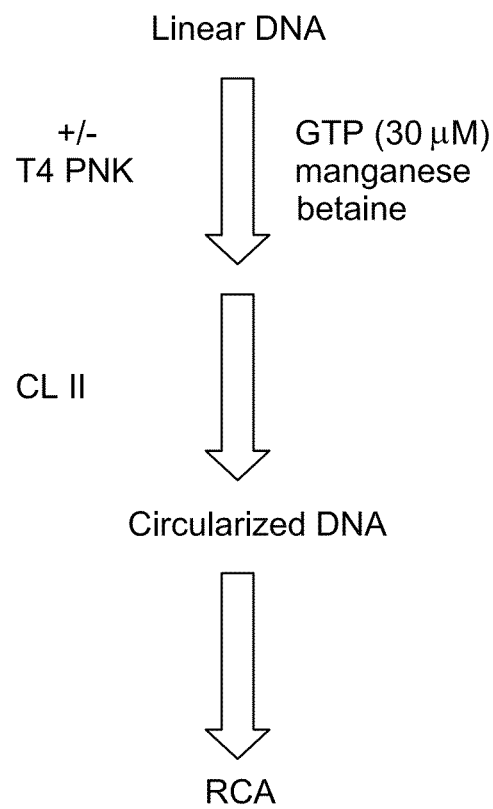
FIG. 9 illustrates a schematic representation of a single-tube reaction of ligase-assisted amplification of fragmented DNA employing PNK and CIRCLIGASE II™ in the presence of GTP.

In some embodiments, phosphorylation repair of the fragmented dsDNA may be performed by using a T4 PNK kinase. The phosphorylation repair may either be performed on the fragmented dsDNA or on the denatured fragmented ssDNA. If the phosphorylation repair is performed on the dsDNA, repaired dsDNA may then be denatured to linear ssDNA, which may be subsequently circularized using a CIRCLIGASE II™ (abbreviated as CLII). CIRCLIGASE II™ comprises a substantially adenylated form of TS2126 RNA ligase. Template-independent intra-molecular ligation of ssDNA by CIRCLIGASE II™ is inhibited by higher concentrations of ATP or dATP. However, the phosphorylation repair by kinase often requires the presence of ATP. Further, it may not be easy to remove ATP from the reaction mixture without damaging the DNA. For example, a phosphatase treatment of the reaction mixture to remove ATP will also result dephosphorylation of DNA (unless the DNA is protected, for example, by pre-adenylation), thus making the DNA strands un-ligatable. As a result, performing a phosphorylation repair of the fragmented DNA and generation of ssDNA circles in a single tube without any intervening purification or isolation steps is often difficult. The methods provided herein employ GTP, CTP, UTP or dTTP instead of ATP during the kinase reaction. Since CIRCLIGASE II™ is more tolerant to GTP or an alternate phosphate donor (e.g., CTP or UTP), the kinase repair step and the ligation step may be conducted in a single reaction vessel without any intervening purification and/or isolation steps. The kinase reaction mixture may further comprise additional reagents such as manganese salts and betaine (zwitterionic trimethylglycine). Once ligated, the ssDNA circles may be amplified. By conducting the ligation and amplification reaction at a relatively low concentration of GTP, the single-tube workflow described herein avoids the intermittent clean-up steps between enzymatic treatments and minimizes the DNA template loss (see FIG. 9 for a schematic representation a single-tube workflow involving kinase repair, ligation and amplification).

In some embodiments, an alternative method for generating a single-stranded DNA circle from a linear DNA is provided, wherein the method employs a DNA pre-adenylation step prior to intra-molecular ligation step. First, the linear DNA may be incubated with a polynucleotide kinase in the presence of ATP to generate a ligatable DNA sequence that comprises a phosphate group at 5' terminal end and a hydroxyl group at 3' terminal end. The ligatable DNA sequence is then incubated with an adenylating enzyme in presence of adenosine triphosphate to generate a 5' adenylated DNA sequence. The 5' adenylated DNA sequence has a free 3' hydroxyl group. The concentration of ATP is in the ligation reaction is selected such that no adenylation happens at the 3' end of the ligatable DNA sequence. The 5' adenylated DNA sequence is then incubated with a non-adenylated ligase, which is capable of template-independent intra-molecular ligation of the 5' adenylated DNA sequence, to generate the single-stranded DNA circle. If an ATP-dependent non-adenylated ligase is employed for the intra-molecular ligation reaction, the ATP may have to be removed from the reaction mixture by treating the reaction mixture with a phosphatase prior to the intra-molecular ligation reaction. The 5' phosphate at the terminal nucleotide of the DNA, which would normally be removed by a phosphatase, is protected from the phosphatase treatment because of the pre-adenylation. If the DNA is in double-stranded form, it needs to be denatured prior to intra-molecular ligation reaction. All the steps of the method are performed in single reaction vessel without any intervening isolation or purification steps.

In some embodiments, an RNA ligase such as RNA ligase I derived from thermophilic archeabacteria, *Methanobacterium thermoautotrophicum* (Mth RNA ligase 1) is used in the presence of ATP to generate the adenylated form of the linear DNA. A mutant or suitably engineered ATP-independent ligase that is defective in self-adenylation, de-adenylation and/or adenylate transfer may be used for the intra-molecular ligation reaction of the adenylated linear DNA to generate the single-stranded DNA circle. For example, a motif V lysine mutant (K246A) of Mth RNA ligase may be employed. This mutant has full ligation activity with pre-adenylated substrates. Mth RNA ligase mutant that has an alanine substitution for the catalytic lysine in motif I (K97A) may also be employed. The activity of the K97A mutant is similar with either pre-adenylated RNA or single-stranded DNA (ssDNA) as donor substrates but has a two-fold preference for RNA as an acceptor substrate compared to ssDNA with an identical sequence. If ATP-dependent ligases such as TS2126 RNA ligase are employed for intra-molecular ligation reaction of the 5' adenylated DNA sequences, the ATP in the reaction may have to be removed prior to the ligation reaction.

In some embodiments, ligase-assisted whole-genome amplification employing the alternative workflow is provided. A schematic representation of this workflow is provided in FIG. 11. The method comprises the repair of fragmented DNA with a kinase and pre-adenylating the fragmented DNA at the 5' end with an RNA ligase or DNA ligase in presence of ATP prior to ligation and amplification. Fragmented DNA comprising sequences that have non-ligatable ends (e.g., sequences comprising 5' hydroxyl and/or 3' phosphoryl groups) are phosphorylated at 5' ends and de-phosphorylated at 3' ends by treating with a kinase to generate a ligatable DNA sequence. The ligatable DNA sequence may then adenylated using an RNA ligase such as Mth RNA ligase (MthRnl 1), in the presence of ATP to generate an adenylated form of the fragmented DNA. The ATP is subsequently removed from the reaction mixture by treating the reaction mixture with a phosphatase (e.g., shrimp alkaline phosphatase (SAP)). Any method that is available in the art for 5' adenylation of a DNA may be employed (e.g., RNA ligase, DNA ligase or synthetic methods). The pre-adenylated single-stranded linear DNA is then treated with an RNA ligase that has a low degree of adenylation such as CIRCLIGASE I™ to generate DNA circles via intra-molecular ligation. The DNA circles are then amplified using RCA. In embodiments where CIRCLIGASE I™ to generated DNA circles via intra-molecular ligation, the intra-molecular DNA ligation and subsequent amplification reaction are performed in the absence of ATP. Elimination of ATP from the reaction mixture after kinase treatment and pre-adenylation reaction is essential since circularization of pre-adenylated ssDNA by CIRCLIGASE I™ is inhibited by ATP. In some embodiments, ATP is converted to adenosine and phosphate by treatment with a phosphatase. Even though adenosine is not inhibitory to the circularization reaction, the resultant phosphate may inhibit the intra-molecular ligation reaction. The generated phosphate may be further removed by treating the reaction mixture with phosphate-sequestering enzymes or with reagents that precipitate or remove phosphate (e.g., phosphate binding resin such as LayneRT resin) from the solution. Phosphate removal may also be achieved by treating the reaction mixture with an enzyme such as maltose phosphorylase which catalyzes conversion of maltose to glucose and glucose-1-phosphate, thereby removing the phosphate from the solution. Inclusion of kinase in the reaction allows circularization and amplification of DNA fragments in a pool that does not contain a 5' phosphate and/or 3' hydroxyl groups, thereby creating a more representative library via ligase-assisted amplification. Pre-adenylation of target DNA facilitates the use of ligases having low degree of adenylation (e.g., CIRCLIGASE I™, which is about 30% adenylated) for intra-molecular ligation reaction. This may be of interest since ligases having high degree of adenylation (e.g., CIRCLIGASE II™) ligate un-adenylated DNA only a single time. Thus, a stoichiometric amount of ligase is often required to drive an intra-molecular ligation reaction to completion. In contrast, ligases that have a low degree of adenylation (such as CIRCLIGASE I™) have high turn-over, and can reversibly and catalytically or repeatedly act on multiple pre-adenylated DNA molecules. This increases ligation kinetics, reduces the quantity of ligase required, and potentially allows for increased circularization of more difficult or complex DNA templates.

In some embodiments, methods for ligase-assisted, whole-genome amplification is used for amplification and subsequent detection of circulating nucleic acids (e.g., circulating DNA from the non-cellular fraction of a biological sample) in a biological sample such as whole blood or urine. Circulating nucleic acids may originate from apoptotic or necrotic cells, or may be actively released from cells. Since cellular nucleases break down the high molecular weight genomic DNA into small, nucleosome-sized fragments, circulating nucleic acids are naturally highly fragmented. Highly fragmented circulating nucleic acid is often not amenable for conventional nucleic acid amplification methods. Further, circulating nucleic acids are present in very low quantities in the bloodstream. Standard rolling circle amplification (RCA) of double-stranded circulating linear nucleic acids is inefficient and highly biased. Separating the circulating nucleic acids to single-strands and circularizing with a ligase prior to rolling circle amplification improves efficiency and leads to less bias. To enable good RCA kinetics and high sensitivity with such dilute DNA template, RCA methods employing primers comprising LNAs are employed. This improved RCA has been optimized for trace DNA and single-cell amplification.

In some embodiments, a method of amplifying circulating DNA from the whole blood is provided. Circulating DNA is amplified from the non-cellular fraction of the whole blood (e.g., plasma or serum). This method comprises the steps of collecting the non-cellular fraction of the whole blood, collecting the circulating DNA (mostly presented in its native double-stranded form) from the non-cellular fraction, denaturing the double-stranded DNA to generate linear single-stranded DNA, circularizing the circulating single-stranded DNA molecule to generated single-stranded DNA circles, and amplifying the single-stranded DNA circles via rolling circle amplification. Due to persistence length, it is not generally possible to circularize dsDNA that has a sequence length smaller than 150 bp, and it is very difficult to circularize dsDNA until the DNA is longer than 200 bp. In contrast, linear ssDNA molecules having a sequence length of 15 nucleotides (nt) or more are very efficiently circularized by a suitable ligase as long as the 5' end is phosphorylated and the 3' end is hydroxylated. The circularization of the single-stranded DNA to generate single-stranded DNA circle is achieved by employing a ligase that is capable of template-independent intra-molecular ligation of single-stranded DNA. In some embodiments, the circularization of the single-stranded DNA molecules is performed by treating the single-stranded linear DNA with an RNA ligase such as CIRCLIGASE II™.

In some embodiments, sensitivity of circulating DNA detection is further increased by phosphorylating the circulating nucleic acids with polynucleotide kinase (PNK) prior to the ssDNA ligation step and RCA. Upon incorporating the PNK step in the work flow, ligase-assisted whole-genome amplification methods presented herein could detect male circulating DNA in female whole blood when spiked at 1% levels (triplicate repeats). Template-independent intra-molecular ligation cannot be achieved unless the ssDNA template has a 5' phosphate group and a 3' hydroxyl group. A variety of conditions produce 5' hydroxyls in DNA (including DNase II enzymatic cleavage, and phosphatase activity in blood). The PNK treatment eliminates this problem and improves the diversity of rolling-circle amplified CNA library.

In some embodiments, kits for generation of a single-stranded DNA circle from a linear DNA are provided. In one embodiment, the kit comprises a polynucleotide kinase, a phosphate donor and a pre-adenylated ligase that is capable of template-independent, intra-molecular ligation of ssDNA sequence, packaged together. The polynucleotide kinase may be a T4 PNK. The phosphate donor may be chosen from GTP, UTP, CTP or dTTP. In one embodiment, the kit may include a TS2126 ligase. More than 60% of the TS2126 ligase may be pre-adenylated. The kit may further comprise buffers (e.g., HEPES), DNA amplification regents (e.g., DNA polymerase, primers, dNTPs) and other reagents (e.g., $MnC_2$, betaine) that are employed for the generation of single-stranded DNA circle by the provided methods. In some embodiments, the kit may include a Phi29 DNA polymerase and random/partially constrained primers. In another embodiment, the kit comprises an adenylating enzyme, a phosphatase and a non-adenylated ligase packaged together. The kit may further comprise a polynucleotide kinase and/or a phosphate donor. The adenylating enzyme may be an RNA ligase I derived from *Methanobacterium thermoautotropicum* (Mth RNA ligase). The non-adenylated ligase may be a composition of TS2126 ligase, wherein more than 60% of the ligase is in the non-adenylated form. The kits may further include instruction for generation of single-stranded DNA circle from a linear DNA.

Practice of the invention will be still more fully understood from the following examples, which are presented herein for illustration only and should not be construed as limiting the scope of the present invention as defined by the appended claims. Some abbreviations used in the examples section are expanded as follows: "mg": milligrams; "ng": nanograms; "pg": picograms; "fg": femtograms; "mL": milliliters; "mg/mL": milligrams per milliliter; "mM": millimolar; "mmol": millimoles; "pM": picomolar; "pmol": picomoles; "µL": microliters; "min.": minutes and "h.": hours.

EXAMPLES

Example 1

Whole-Genome Amplification of Circulating Nucleic Acid from Blood Plasma

Figure 2:
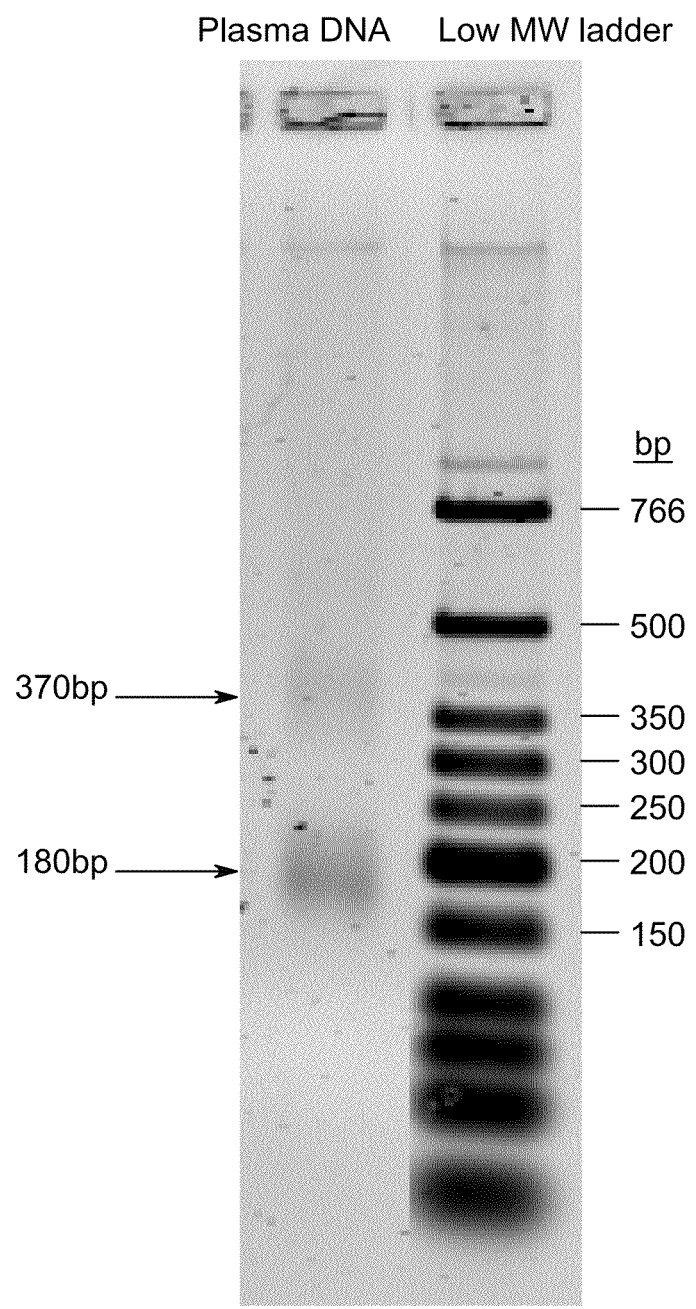
FIG. 2 illustrates size profiles of circulating DNA isolated from blood plasma of healthy individuals.

Circulating DNA was isolated from citrate-phosphate-dextrose (CPD)—stabilized blood plasma of apparently healthy individuals using the Wako DNA extractor SP kit (Wako Pure Chemical Industries). Approximately 1.3 ng was analyzed by electrophoresis through a 2% agarose gel using TBE buffer, stained with SYBR Gold and visualized using a Typhoon imager. As depicted in FIG. 2, the majority of the circulating DNA was approximately 180 bp in length, with an additional smaller amount of sequences that were approximately 370 bp long, and a substantially smaller amount of higher molecular weight sequences.

350 pg circulating DNA from plasma was heated at 95° C. to denature the template. The denatured, single-stranded DNA template was then treated with an RNA or DNA ligase to generated single-stranded DNA circles. ATP-dependent T4 DNA ligase, cell-encoded NAD-dependent *E. coli* DNA ligase or a thermostable RNA ligase (CIRCLIGASE II™) was used for the ligation reaction. 100 pg of DNA ligated single-stranded DNA circles were then subjected to whole-genome amplification using GenomiPhi kit (GE Healthcare) employing a Phi29 DNA polymerase. The amplification was performed using the primer mixture+N+N(at N)(at N)(at N)*N where the "at N" represents a random mixture containing 2-amino dA, 2-thio-dT, normal G and normal C. Real-time amplification was performed by adding a small amount of SYBR green I to the amplification mixture and monitoring the fluorescence signal increase over time in a Tecan plate reader (Tecan SNiPer, Amersham-Pharmacia Biotech). For comparison, an equivalent concentration of un-treated genomic DNA, untreated plasma DNA, and a sample without DNA template (No template amplification) were included.

Figure 3A:
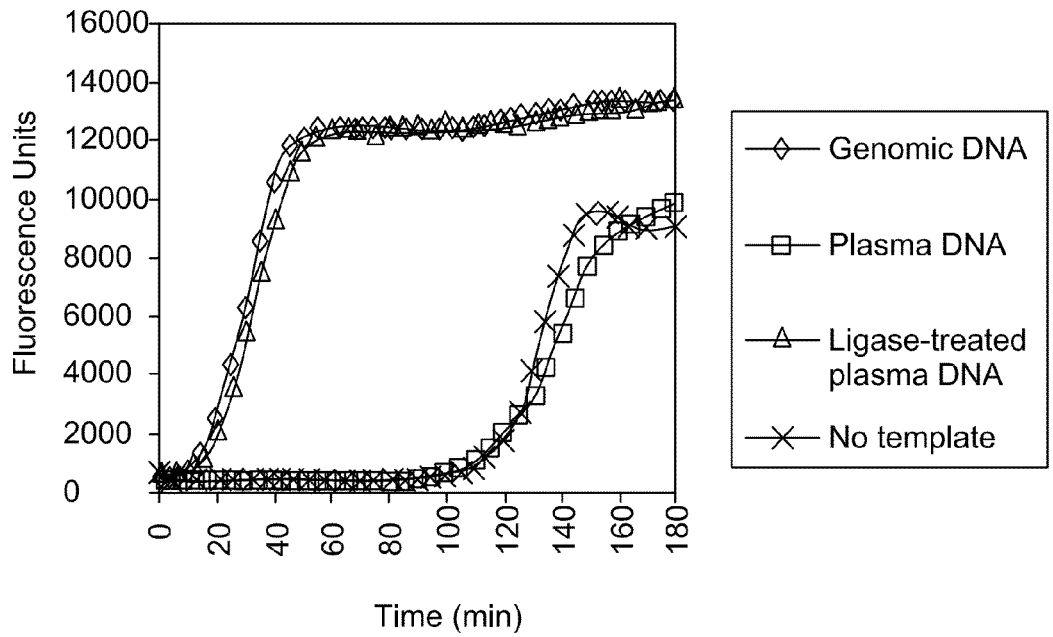
FIG. 3A illustrates a ligase-assisted whole-genome amplification of circulating DNA extracted from the non-cellular fraction of whole blood, using CIRCLIGASE II™.
Figure 3B:
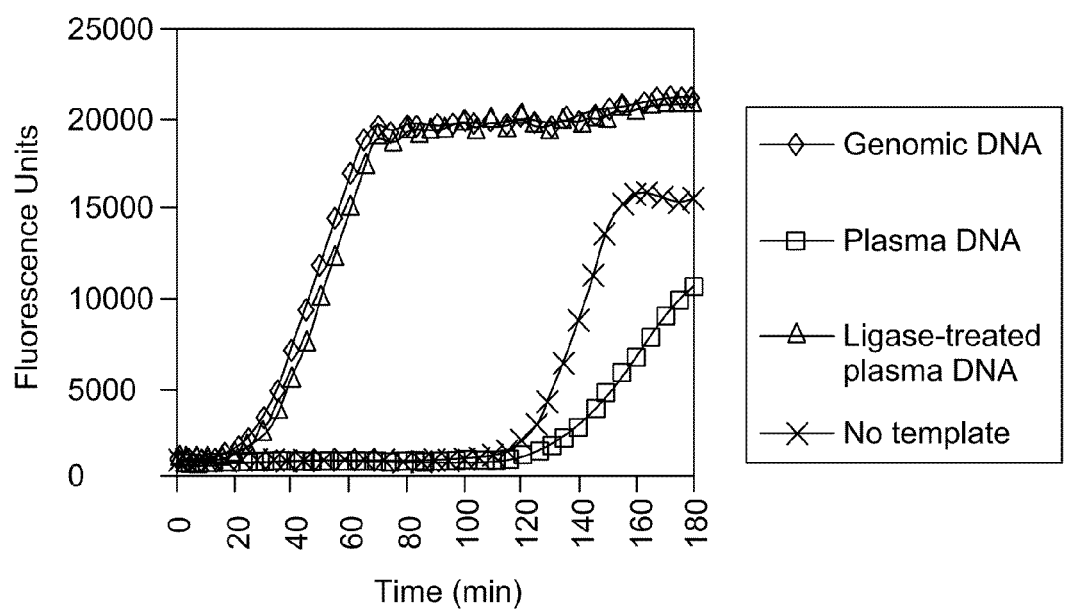
FIG. 3B illustrates a ligase-assisted whole-genome amplification of circulating DNA extracted from the non-cellular fraction of whole blood, using T4 DNA ligase.
Figure 3C:
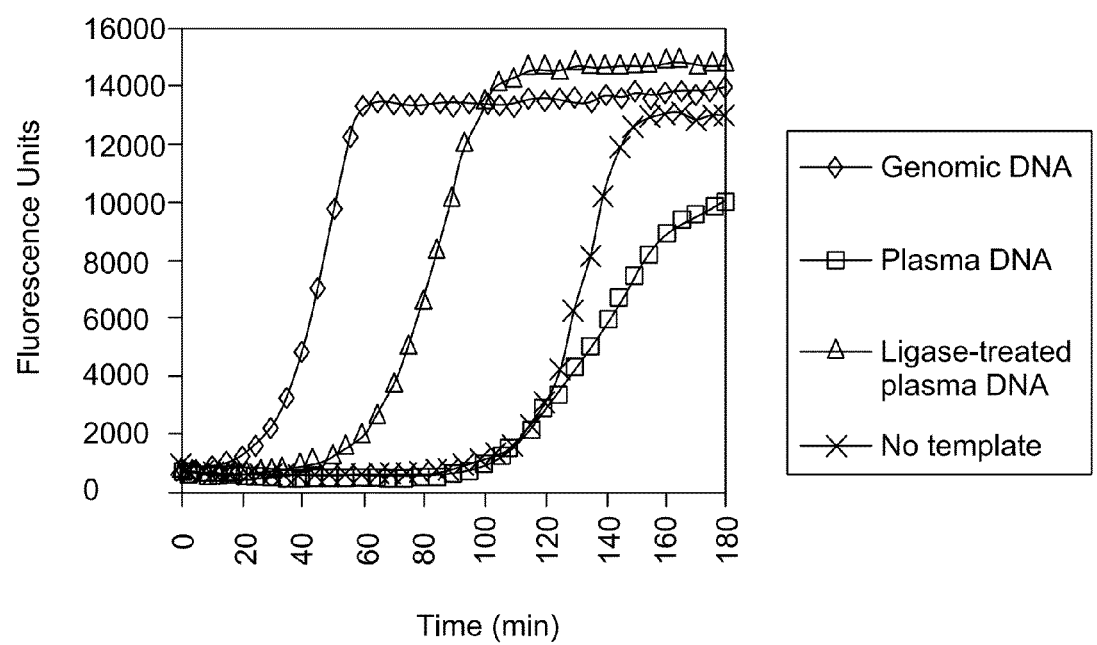
FIG. 3C illustrates a ligase-assisted whole-genome amplification of circulating DNA extracted from the non-cellular fraction of whole blood, using *E. Coli* DNA ligase.

As depicted in FIG. 3, the amplification kinetics of the untreated, fragmented plasma DNA were much lower when compared to an equivalent amount of high molecular weight genomic DNA, indicating a defect in amplification. However, when the fragmented plasma DNA was pre-treated and converted to single-stranded DNA circles using the CIRCLIGASE II™, rapid amplification kinetics were achieved (FIG. 3A). The ligases, including the ATP-dependent T4 DNA ligase (FIG. 3B) and the cell-encoded NAD-dependent *E. coli* DNA ligase (FIG. 3C) were also effective, but with less efficiency, in restoring amplification kinetics of the fragmented plasma DNA. In these examples, the relative increase in amplification kinetics indicates the effectiveness of each of the ligases in promoting the intra-molecular ligation of the single-stranded DNA template.

Example 2

Figure 4:
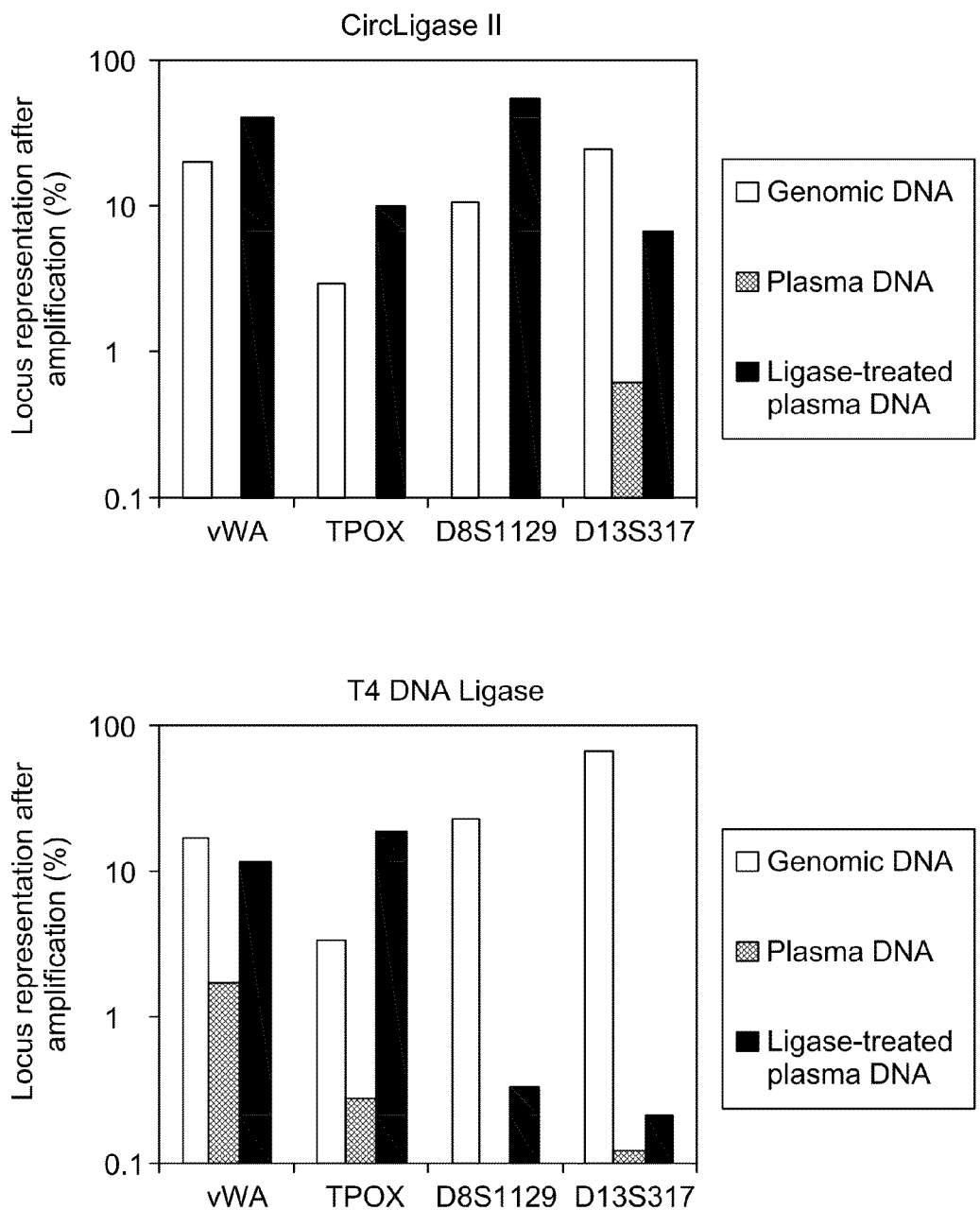
FIG. 4 illustrates the effectiveness of ligase-assisted whole-genome amplification for sensitive and balanced DNA amplification of four different CODIS loci.

Analysis of Amplified Circulating Nucleic Acids from Blood Plasma by Ligase-Assisted Whole-Genome Amplification The amplified DNA generated in Example 1 was further analyzed by quantitative PCR using primers targeting four different CODIS loci (vWA, TPDX, D8S1129, and D13S317) to sample the effectiveness of the ligase-assisted whole-genome amplification method for promoting sensitive and balanced DNA amplification. These DNA levels were compared with the values from unamplified DNA to determine the relative representation levels after amplification. As illustrated in FIG. 4, in both examples, the amplification of untreated plasma DNA led to sequence dropout or produced DNA that was highly under-represented at the tested loci. In contrast, including either CIRCLIGASE II™ or T4 DNA ligase in the method prevented the sequence dropout of the four loci and produced DNA that was more similar in representation to the amplified high molecular weight genomic DNA. In the example using CIRCLIGASE II™ as the single-stranded DNA ligase, out of 12 different CODIS loci tested by quantitative PCR (qPCR) using primers targeting 12 different CODIS loci, 11 were recovered after amplification, whereas only 4 were present in the amplified untreated plasma DNA (FIG. 5). In FIG. 5, the Ct values reported are an average of two replicates. PCR reactions where the Ct value was undetermined are marked by an "X".

Example 3

Figure 6:
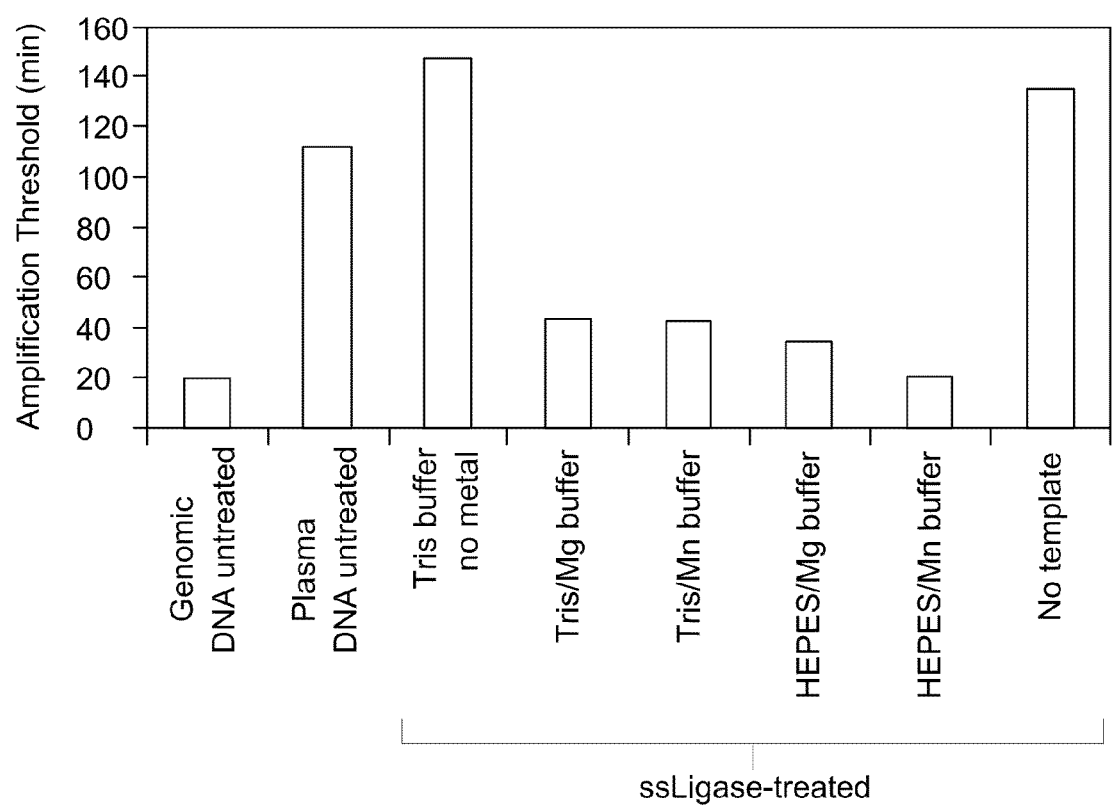
FIG. 6 illustrates the efficiencies of ligase-assisted whole-genome amplification in different reaction and buffer conditions.

Optimization of Reaction Conditions for Ligase-Assisted Whole-Genome Amplification The ligase-assisted DNA amplification reaction was further optimized by optimizing the efficiency of ligation reaction of single stranded DNA molecule by TS2126 RNA ligase. The presence of metal ion was essential for the ligation reaction since eliminating manganese from the standard manufacturer recommended buffer reduced amplification rates to background levels. Untreated genomic DNA and untreated plasma DNA were compared with CIRCLIGASE II™-treated plasma DNA samples using modified buffer conditions (FIG. 6). All buffer conditions contained 33 mM KOAc, 0.5 mM DTT, and 1M betaine. Where indicated, buffers contained 33 mM Tris-acetate (pH 7.5) or 33 mM HEPES-KOH (pH 8.0) and additionally contained 2.5 mM $MgCl_2$ or 2.5 mM $MnCl_2$. Real-time amplification was performed by adding a small amount of SYBR green I to the amplification mixture and monitoring fluorescence increase over time in a Tecan plate reader. The amplification threshold is the time at which fluorescence rises above background levels (2000 RFU).

Comparison of amplification kinetics of ligase-assisted whole-genome amplification reactions (100 pg samples) is depicted in FIG. 6. Both magnesium and manganese promoted similar effects in the presence of the standard TRIS buffer, but it was observed that the combination of manganese and magnesium in the presence of HEPES buffer, pH 8.0 was most effective in promoting high amplification rates. HEPES buffer increased circularization efficiency of the plasma DNA in this reaction condition may be due reduced oxidation of the manganese cation in the HEPES buffer.

Example 4

Figure 7:
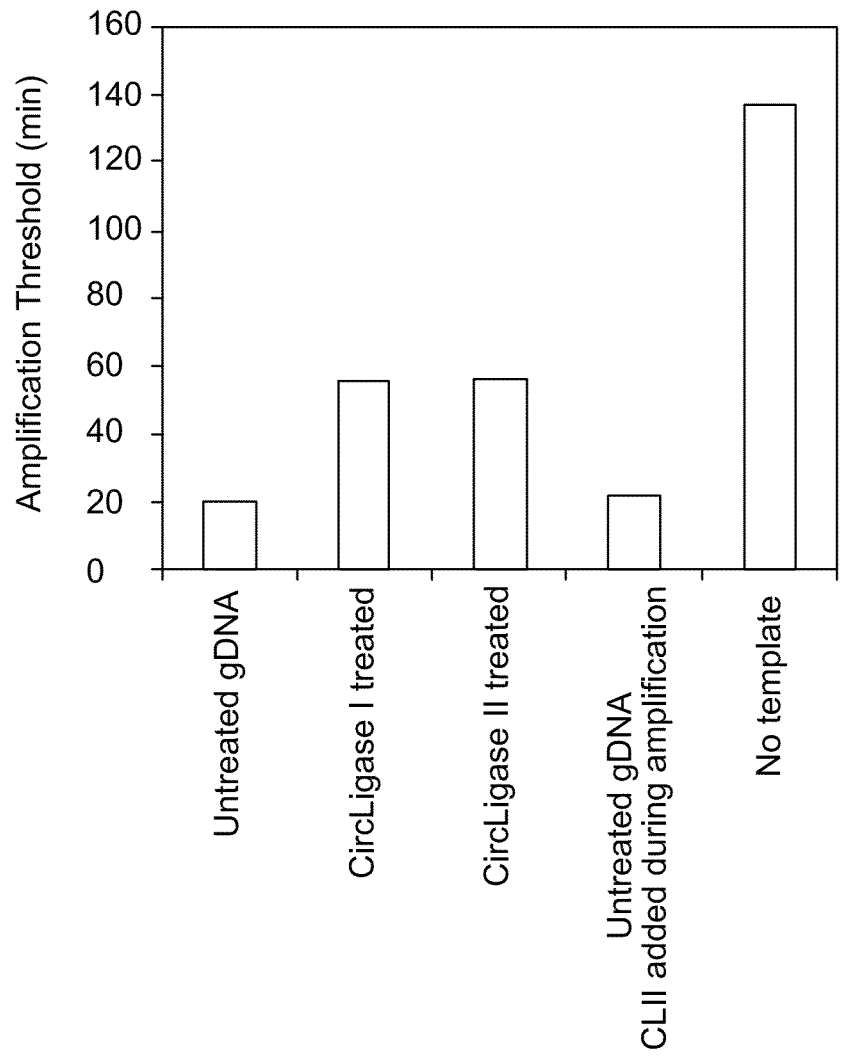
FIG. 7 illustrates the inhibition of amplification of high molecular weight genomic DNA in ligase-assisted whole-genome amplification.

Inhibition of Amplification of High Molecular Weight Genomic DNA in Ligase-Assisted Whole-Genome Amplification The amplification kinetics of whole-genome amplification reactions of untreated genomic DNA was compared with CIRCLIGASE I™ and CIRCLIGASE II™-treated genomic DNA samples (100 pg samples). The results are illustrated in FIG. 7. As depicted in FIG. 7, CIRCLIGASE™ treatment of genomic DNA produced an inhibitory effect on the amplification rate of high molecular weight genomic DNA (unlike the positive effects on plasma DNA). The inhibition was apparent for both CIRCLIGASE I™ and CIRCLIGASE II™.

To investigate if Phi29-based amplification was inhibited by the ligase, untreated genomic DNA was amplified in the presence of active ligase. Real-time amplification was performed by adding a small amount of SYBR green I to the amplification mixture and monitoring fluorescence increase over time in a Tecan plate reader. Amplification threshold is the time at which fluorescence rises above background levels (2000 RFU). It was observed that the genomic DNA amplification inhibition was not an effect of active ligase being present during the amplification.

A preference for the amplification of circulating over high molecular weight genomic DNA might be an advantage for certain applications, as genomic DNA from blood cells often contaminates preparations of circulating nucleic acids, and is of less diagnostic value.

Example 5

Single-Tube Amplification of Fragmented DNA Employing Ligase-Assisted Whole-Genome Amplification—Effect of Phosphorylation of Circulating DNA Fragments with Kinase Prior to Intra-Molecular Ligation Phosphorylation of circulating DNA fragments with kinase allowed more sensitive detection of circulating DNA in blood plasma. A male-female plasma/blood mixing experiment was performed to establish that the library created from the input DNA treated with kinase was more representative, allowing for more sensitive detection of the DYS14 male-specific marker (FIG. 10, ⅔ replicates, whereas only ⅓ was detected if phosphorylation was not done). 100 µL of blood/plasma mixtures were prepared as follows: 100 A: 100% male plasma; 5A-C: male plasma spiked into female whole blood at 5% v/v; 1A-C: male plasma spiked into female whole blood at 1% v/v; and 0 A: 100% female blood. The plasma was separated from the blood cells by lateral flow through an MF1 membrane (Whatman) followed by collection onto a cellulose pad that was dried and stored overnight. The circulating DNA was then isolated from the cellulose pad by a modification of the Wako extractor SP kit (Wako Pure Chemical Industries), a standard sodium iodide/detergent based method. Approximately 1.8 ng of DNA was then treated with or without T4 polynucleotide kinase in the presence of GTP, manganese, and betaine and then treated with CIRCLIGASE II™ to circularize the single-stranded DNA fragments. DNA was then subjected to GenomiPhi whole-genome amplification (GE Healthcare) and products were analyzed by quantitative PCR to assess the detection of two markers: Dys14, which is a multi-copy gene located on the Y-chromosome and should be detectible from the male fraction only, and D16S539 which is an STR locus located on chromosome 16 and should be detectible from both male and female fractions. The reaction was performed in a single reaction vessel, without any intermediate purification or isolation steps in the workflow. This was achieved by performing the phosphorylation reaction at a relatively low concentration of GTP.

Figure 10:
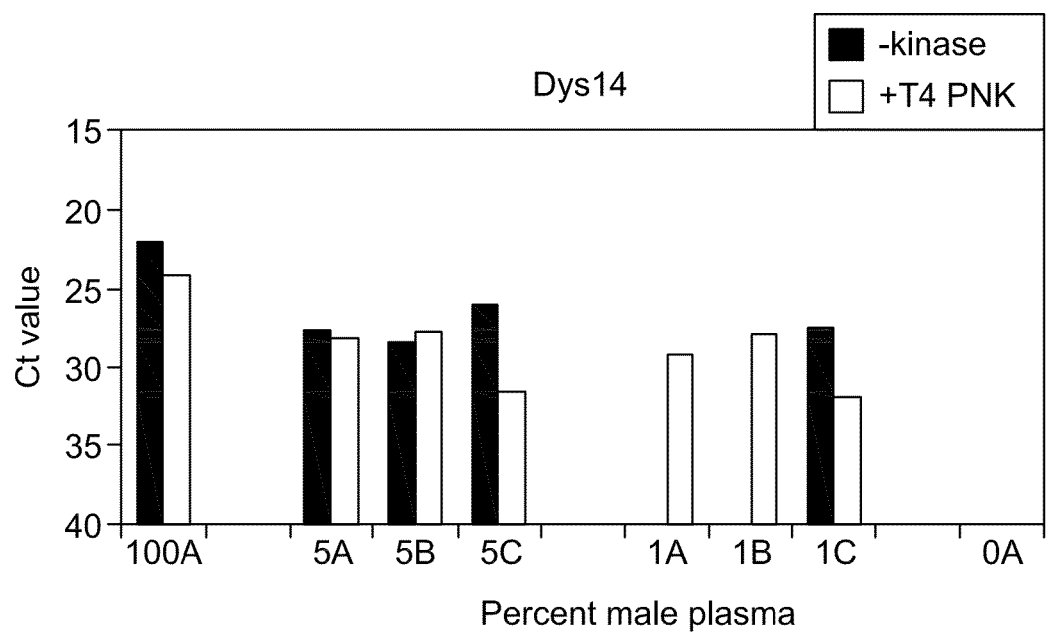
FIG. 10 illustrates a single-tube ligase-assisted amplification reaction using male-female plasma/blood, wherein DYS14 male-specific marker is detected using a library created from the input DNA.
Figure 10:
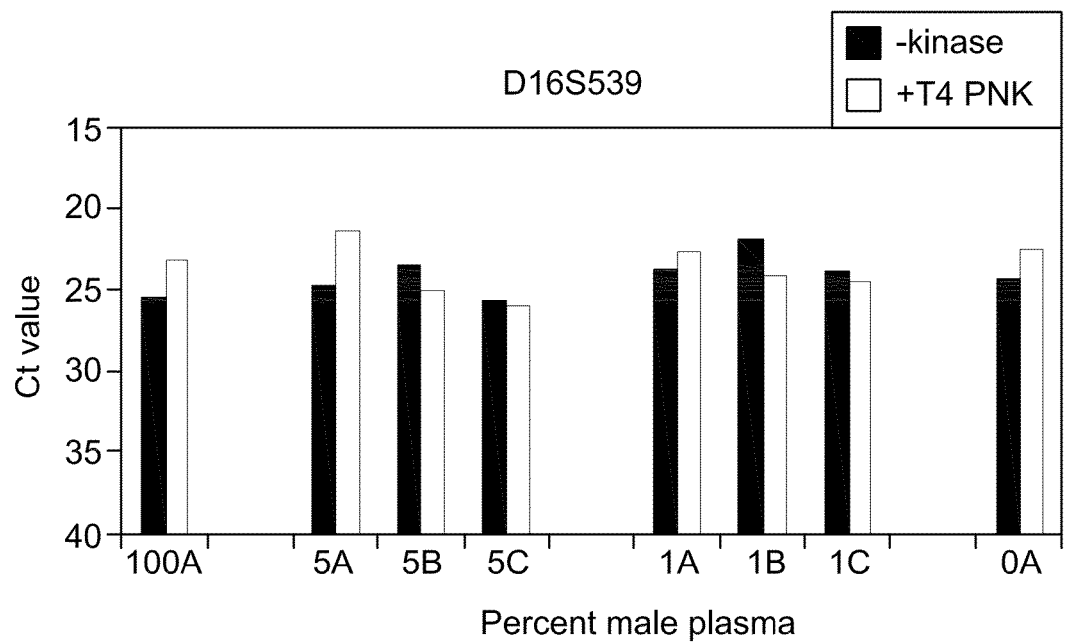

FIG. 10 illustrates that inclusion of a kinase in the reaction allows the circularization and amplification of DNA fragments in a pool that do not contain a 5' phosphate, thereby creating a more representative library. This would include DNA fragments containing a 5' hydroxyl, which are specifically generated by DNase II digestion during cell death. Using a male-female plasma/blood mixing experiment, it is demonstrated that the library created from the input DNA treated with kinase was more representative, allowing for more sensitive detection of the DYS14 male-specific marker (3/3 replicates, whereas only ⅓ was detected if phosphorylation was not done).

Example 6

Effect of Pre-Adenylation of Fragmented DNA Prior to Circularization Reaction

Figure 12:
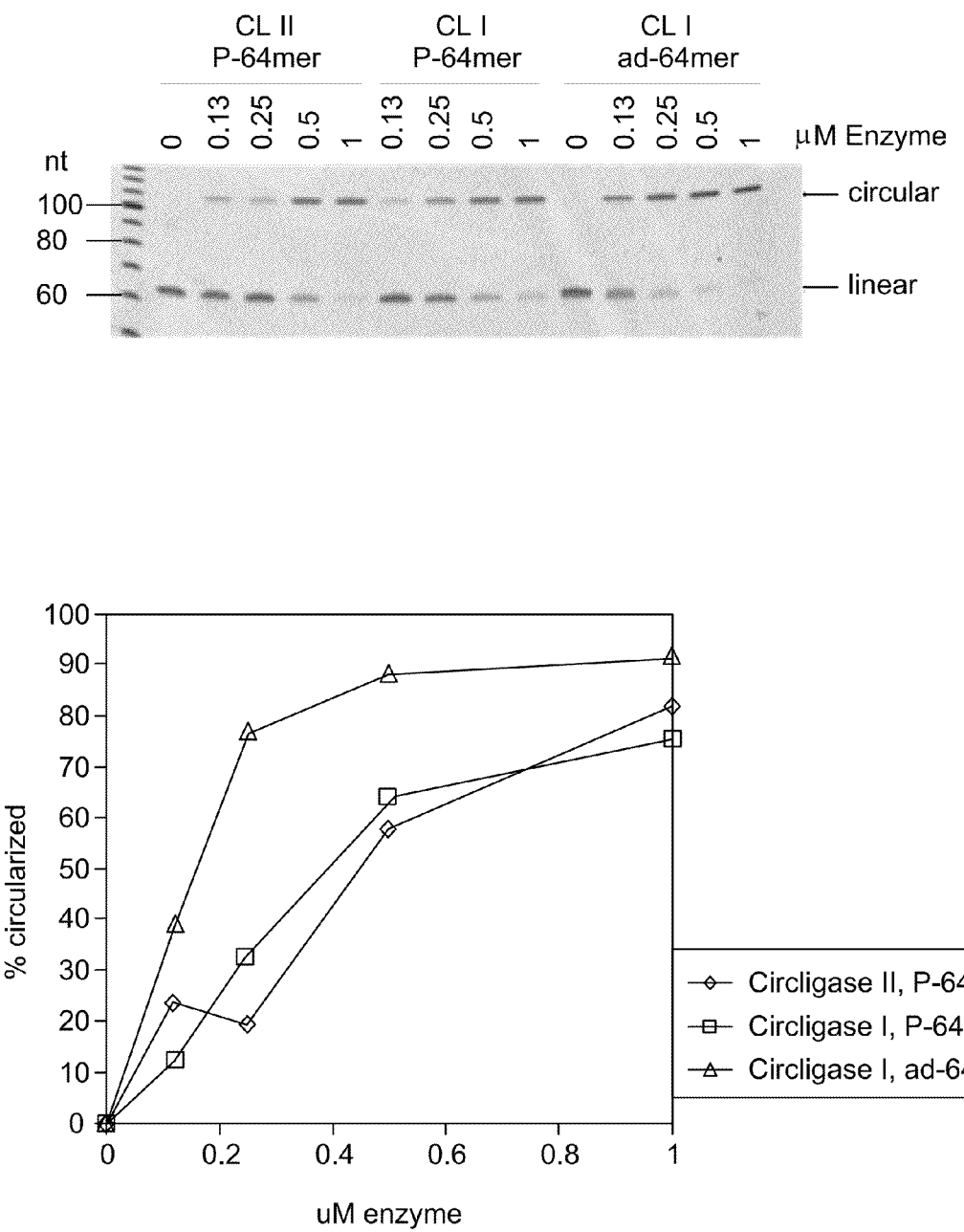
FIG. 12 illustrates the enhanced efficiency of circularization of a pre-adenylated DNA sequence using a substantially non-adenylated ligase.

The efficiency of circularization of a small DNA fragment that is either phosphorylated or pre-adenylated in 40 minutes is assessed with different amounts of CIRCLIGASE™ enzyme. 2.5 pmol of a 64-mer oligonucleotide containing either a phosphate group or an adenylation at the 5' position was treated with increasing amounts of CIRCLIGASE I™ or CIRCLIGASE II™ for 40 minutes at 60° C. The percent circularization was determined by scanning the intensity of the bands at the linear and circular positions. As depicted in FIG. 12, pre-adenlyation of fragmented DNA improved the ligation and amplification kinetics. In FIG. 12, P-64mer represents a 5'-phosphorylated 64-nt oligonucleotide; and ad-64 represents pre-adenylated 64-nt oligonucleotide. Pre-adenylated DNA was circularized more rapidly than the standard phosphorylated DNA. Further, the ligation enzyme, which has low degree of adenylation catalyzed the ligation of a molar excess of substrate indicating that the ligase has multiple opportunities to ligate the pre-adenylated DNA molecule, which increases ligation kinetics and potentially allows for increased circularization of more difficult templates.

Example 7

Figure 13:
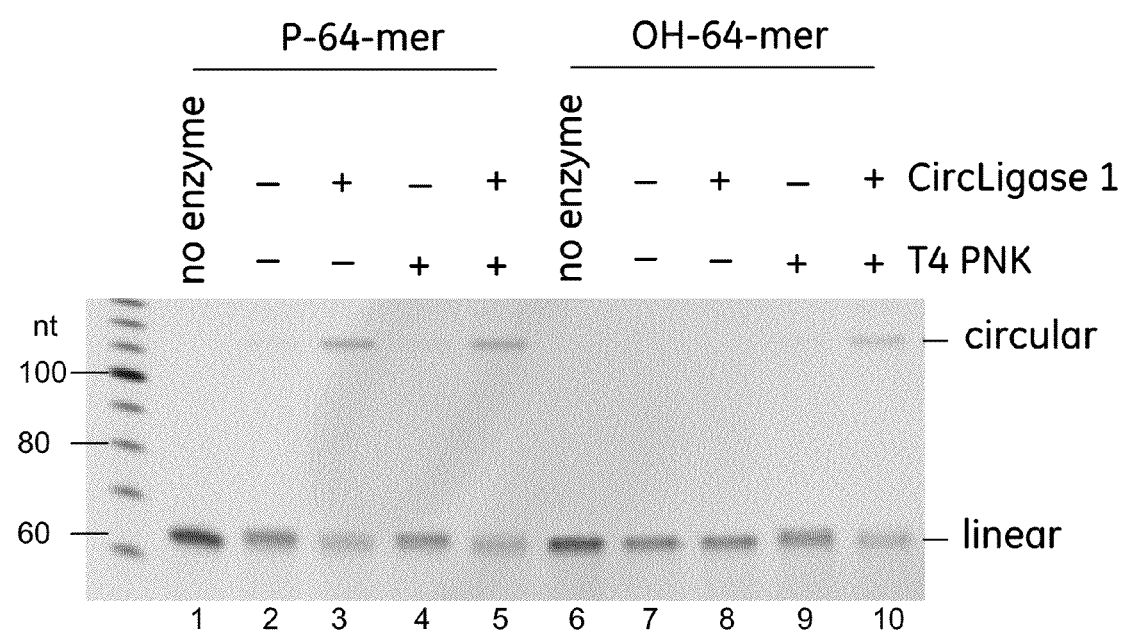
FIG. 13 illustrates the enhanced efficiency of ligase-assisted whole-genome amplification when the target DNA sequence was pre-adenylated and when the ligation was performed using a non-adenylated ligase.

Circularization of 5'-Phosphate and 5'-Hydroxyl-Containing Oligonucleotides Using the Pre-Adenylation Workflow Reactions containing 5 pmol of a 64-mer oligonucleotide with either a phosphate group or a hydroxyl group at the 5' position were treated with 1.25 U of T4 polynucleotide kinase at 37° C. where indicated. Following incubation with 25 pmol Mth RNA ligase at 65° C., reactions were treated with 0.25 units of shrimp alkaline phosphatase. Since Mth RNA ligase is very sensitive to ATP concentration, at standard 100 µM ATP concentration, Mth RNA ligase almost exclusively adenylate DNA ends. No intra-molecular ligation happens by Mth RNA ligase at this ATP concentration. Enzymes were heat-inactivated after each incubation. Finally, reactions were treated with 50 units of CIRCLIGASE I™ where indicated and incubated for 60 minutes at 60° C. The percent circularization was determined by scanning the intensity of the bands at the linear and circular positions (FIG. 13). P-64mer represents a 5'-phosphorylated 64-nt oligonucleotide and ad-64mer represents a pre-adenylated 64-nt oligonucleotide.

Figure 11:
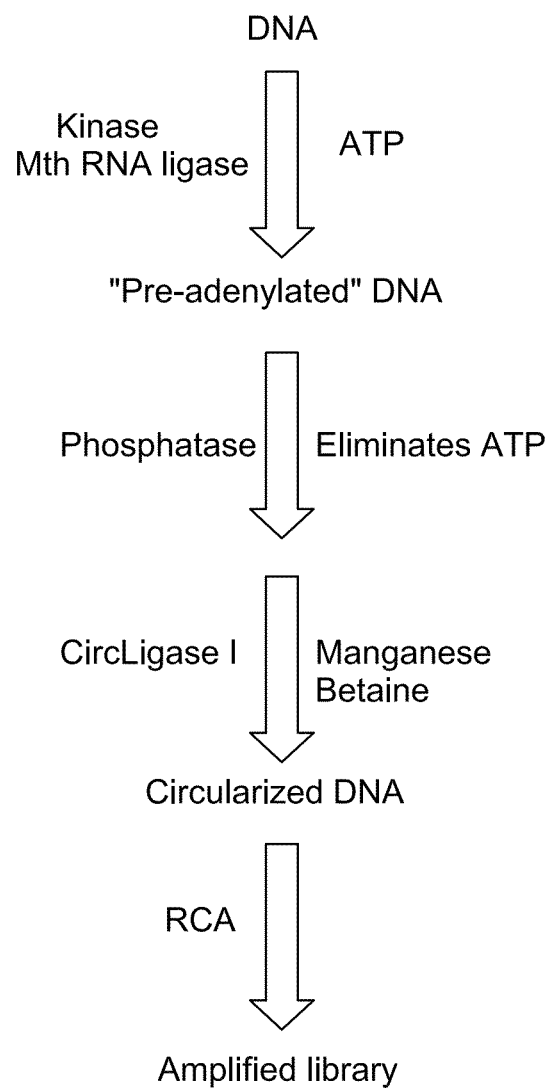
FIG. 11 illustrates a schematic representation of phosphorylation and pre-adenlyation of fragmented DNA followed by ligation using a substantially non-adenylated ligase.

FIG. 11 shows a "single-tube" pre-adenylation workflow in which linear oligonucleotides containing a 5'-phosphate or a 5'-hydroxyl group are converted to circular forms. In this "single-tube" process substrates are successively treated with polynucleotide kinase, Mth RNA ligase, shrimp alkaline phosphatase, and CIRCLIGASE I™ without any intermediate purification steps.

The claimed invention may be embodied in other specific forms without departing from the spirit or essential characteristics thereof. The foregoing embodiments are selected embodiments or examples from a manifold of all possible embodiments or examples. The foregoing embodiments are therefore to be considered in all respects as illustrative rather than limiting on the invention described herein. While only certain features of the claimed invention have been illustrated and described herein, it is to be understood that one skilled in the art, given the benefit of this disclosure, will be able to identify, select, optimize or modify suitable conditions/parameters for using the methods in accordance with the principles of the present invention, suitable for these and other types of applications. The precise use, choice of reagents, choice of variables such as concentration, volume, incubation time, incubation temperature, and the like may depend in large part on the particular application for which it is intended. It is, therefore, to be understood that the appended claims are intended to cover all modifications and changes that fall within the true spirit of the invention. Further, all changes that come within the meaning and range of equivalency of the claims are intended to be embraced therein.

The invention claimed is:

1. A method for generating a single-stranded DNA circle from a linear DNA, the method comprising:
   (a) providing the linear DNA;
   (b) incubating the linear DNA with a polynucleotide kinase in the presence of a phosphate donor to generate a ligatable DNA sequence having a phosphate group at a 5' terminal end and a hydroxyl group at a 3' terminal end; and
   (c) incubating the ligatable DNA sequence with a ligase that is capable of template-independent, intra-molecular ligation of a single-stranded DNA sequence to generate the single-stranded DNA circle,
   wherein all the steps of the method are performed in a single reaction vessel without any intervening isolation or purification steps.

2. The method of claim 1, wherein step (b) is performed using a phosphate donor other than adenosine triphosphate or deoxyadenosine triphosphate.

3. The method of claim 2, wherein the phosphate donor is selected form the group consisting of guanosine triphosphate, cytidine triphosphate, uridine triphosphate, deoxythymidine triphosphate and combinations thereof.

4. The method of claim 3, wherein the phosphate donor is guanosine triphosphate.

5. The method of claim 4, wherein the linear DNA is incubated with the polynucleotide kinase in the presence of less than 200 µM of guanosine triphosphate.

6. The method of claim 5, wherein the linear DNA is incubated with the polynucleotide kinase in the presence of up to 30 µM of guanosine triphosphate and up to 2.5 mM of manganese ion.

7. The method of claim 4, further comprising denaturing the ligatable DNA sequence prior to step (c) if the ligatable DNA sequence is in double-stranded form.

8. The method of claim 7, wherein the ligase is a pre-adenylated ligase.

9. The method of claim 8, wherein the pre-adenylated ligase is a pre-adenylated TS2126 RNA ligase.

10. The method of claim 9, wherein steps (a) to (c) are performed in a sequential manner in the single reaction vessel.

11. The method of claim 10, wherein all the steps of the method are performed in the absence of adenosine triphosphate or deoxyadenosine triphosphate.

12. The method of claim 11, wherein all the steps of the method are performed in HEPES buffer.

13. The method of claim 1, wherein the linear DNA is selected from the group consisting of a circulating DNA, a DNA isolated from formalin fixed paraffin-embedded samples, a forensic DNA sample that have been exposed to environmental conditions, and an ancient DNA sample.

14. The method of claim 1, further comprising amplifying the single-stranded DNA circle under isothermal conditions.

15. The method of claim 14, wherein the single-stranded DNA circle is amplified via rolling circle amplification.

16. The method of claim 15, wherein the rolling circle amplification is performed using a nuclease-resistant primer.

17. The method of claim 16, wherein the nuclease-resistant primer comprises at least one modified nucleotide.

18. The method of claim 15, wherein the single-stranded DNA circle is amplified using a random primer mixture.

19. The method of claim 15, wherein the single-stranded DNA circle is amplified using a primer solution that consists essentially of a partially constrained primer mixture comprising a terminal mismatch primer-dimer structure.

20. A method of generating a single-stranded DNA circle from a linear DNA, the method comprising:
   (a) providing the linear DNA;
   (b) optionally incubating the linear DNA with a polynucleotide kinase in the presence of adenosine triphosphate to generate a ligatable DNA sequence having a phosphate group at a 5' terminal end and a hydroxyl group at a 3' terminal end;
   (c) incubating the linear DNA sequence or the ligatable DNA sequence with an adenylating enzyme in the presence of adenosine triphosphate to generate a 5' adenylated DNA sequence; and
   (d) incubating the 5' adenylated DNA sequence with a non-adenylated ligase, which is capable of template-independent intra-molecular ligation of a 5' adenylated, single-stranded DNA sequence to generate the single-stranded DNA circle,
   wherein all the steps of the method are performed in single reaction vessel without any intervening isolation or purification steps.

21. The method of claim 20, further comprising denaturing the 5' adenylated DNA sequence prior to step (d) if the 5' adenylated DNA sequence is in double-stranded form.

22. The method of claim 21, wherein the adenylating enzyme is an RNA ligase 1 derived from thermophilic archeabacteria, *Methanobacterium thermoautotrophicum*.

23. The method of claim 22, wherein the non-adenylated ligase is a mutant or engineered ligase, which is adenosine-triphosphate-independent and is defective in self-adenlyation, de-adenylation and adenylate transfer.

24. The method of claim 23, wherein the mutant ligase is a mutant of RNA ligase 1 derived from thermophilic archeabacteria, *Methanobacterium thermoautotrophicum*.

25. The method claim 22, further comprising incubating the reaction mixture of step (c) comprising the 5' adenylated DNA sequence with a phosphatase to eliminate the adenosine triphosphate from the reaction mixture.

26. The method of claim 25, wherein the non-adenylated ligase is a TS2126 RNA ligase derived from *thermus* bacteriophage, TS2126.

27. The method of claim 26, wherein steps (a) to (d) are performed in a sequential manner in the single reaction vessel.

28. The method of claim 20, wherein the linear DNA is selected from the group consisting of a circulating DNA, a DNA isolated from formalin fixed paraffin-embedded samples, a forensic DNA sample that have been exposed to environmental conditions, and an ancient DNA sample.

29. The method of claim 20, further comprising amplifying the single-stranded DNA circle under isothermal conditions.

30. The method of claim 29, wherein the single-stranded DNA circle is amplified via rolling circle amplification.

31. The method of claim 30, wherein the single-stranded DNA circle is amplified using a nuclease-resistant primer.

32. The method of claim 31, wherein the nuclease-resistant primer comprises at least one modified nucleotide.

33. The method of claim 30, wherein the single-stranded DNA circle is amplified using a random primer mixture.

34. The method of claim 30, wherein the single-stranded DNA circle is amplified using a primer solution that consists essentially of a partially constrained primer mixture comprising a terminal mismatch primer-dimer structure.

* * * * *